United States Patent [19]

Tedders et al.

[11] Patent Number: 5,718,377
[45] Date of Patent: Feb. 17, 1998

[54] BENEFICIAL INSECT EGG SPRAYING DEVICE

[75] Inventors: Walker Louis Tedders; John L. Blythe, both of Perry, Ga.

[73] Assignee: The United States of America as represented by the Secretary of Agriculture, Washington, D.C.

[21] Appl. No.: 423,765

[22] Filed: Apr. 18, 1995

[51] Int. Cl.[6] .................................................. B05B 9/00
[52] U.S. Cl. ........................ 239/8; 239/77; 239/143; 239/151; 47/1.01
[58] Field of Search ............................. 239/1, 77, 99, 239/101, 147, 151, 159, 163, 170, 171, 172, 754, 144, 8, 143; 111/118, 129; 47/1.01; 43/132.1, DIG. 900

[56] References Cited

U.S. PATENT DOCUMENTS

| | | | |
|---|---|---|---|
| 1,490,522 | 4/1924 | Stocker | 239/172 X |
| 2,401,431 | 6/1946 | Lewis | 239/151 X |
| 2,738,226 | 3/1956 | Bals | 239/77 |
| 2,923,440 | 2/1960 | Ve Horn | 239/143 X |
| 3,708,089 | 1/1973 | Holder et al. | 222/396 |
| 3,847,113 | 11/1974 | Andreev et al. | 118/40 |
| 3,900,165 | 8/1975 | Parke | 239/375 |
| 3,968,933 | 7/1976 | Waldrum | 239/171 |
| 3,994,437 | 11/1976 | Kitterman | 239/1 |
| 4,026,469 | 5/1977 | Frankel et al. | 239/78 |
| 4,260,108 | 4/1981 | Maedgen et al. | 239/171 |
| 4,262,846 | 4/1981 | Funkhouser | 239/1 |
| 4,277,364 | 7/1981 | Shasha et al. | 252/316 |
| 4,348,492 | 9/1982 | Shasha et al. | 524/52 |
| 4,350,266 | 9/1982 | Hetherington et al. | 222/40 |
| 4,382,813 | 5/1983 | Shasha | 71/88 |
| 4,401,273 | 8/1983 | Olson | 239/498 |
| 4,439,488 | 3/1984 | Trimnell et al. | 428/402.24 |
| 4,582,258 | 4/1986 | Olson | 239/498 |
| 4,859,377 | 8/1989 | Shasha et al. | 264/4.1 |
| 4,925,096 | 5/1990 | Gill | 239/172 X |
| 4,966,329 | 10/1990 | Show | 239/144 X |
| 5,061,697 | 10/1991 | Shasha et al. | 514/60 |
| 5,148,989 | 9/1992 | Skinner | 239/8 X |
| 5,269,461 | 12/1993 | Davis | 239/77 |

FOREIGN PATENT DOCUMENTS

| | | | |
|---|---|---|---|
| 1116467 | 12/1959 | Germany | 239/77 |
| 141095 | 6/1919 | United Kingdom | 239/159 |

OTHER PUBLICATIONS

Dreistadt et al., Entomophaga 31(4):397–400 (1986).

Primary Examiner—Andres Kashnikow
Assistant Examiner—Steven J. Ganey
Attorney, Agent, or Firm—Gail E. Poulos; M. Howard Silverstein; John Fado

[57] ABSTRACT

A device for spraying beneficial insect eggs directly onto plants is disclosed which has an air system, an aqueous solution system, a compressed air system for pressurization and agitation, a pressure release system, a tank assembly, and a remote control assembly. There are three different air systems suitable for spraying trees, plants of moderate height or row crops; two different aqueous solution systems, one for spraying moderate height plants and row crops and one for spraying trees. The device provides an economical and alternative strategy for the delivery of beneficial insect eggs to agricultural commodities.

9 Claims, 17 Drawing Sheets

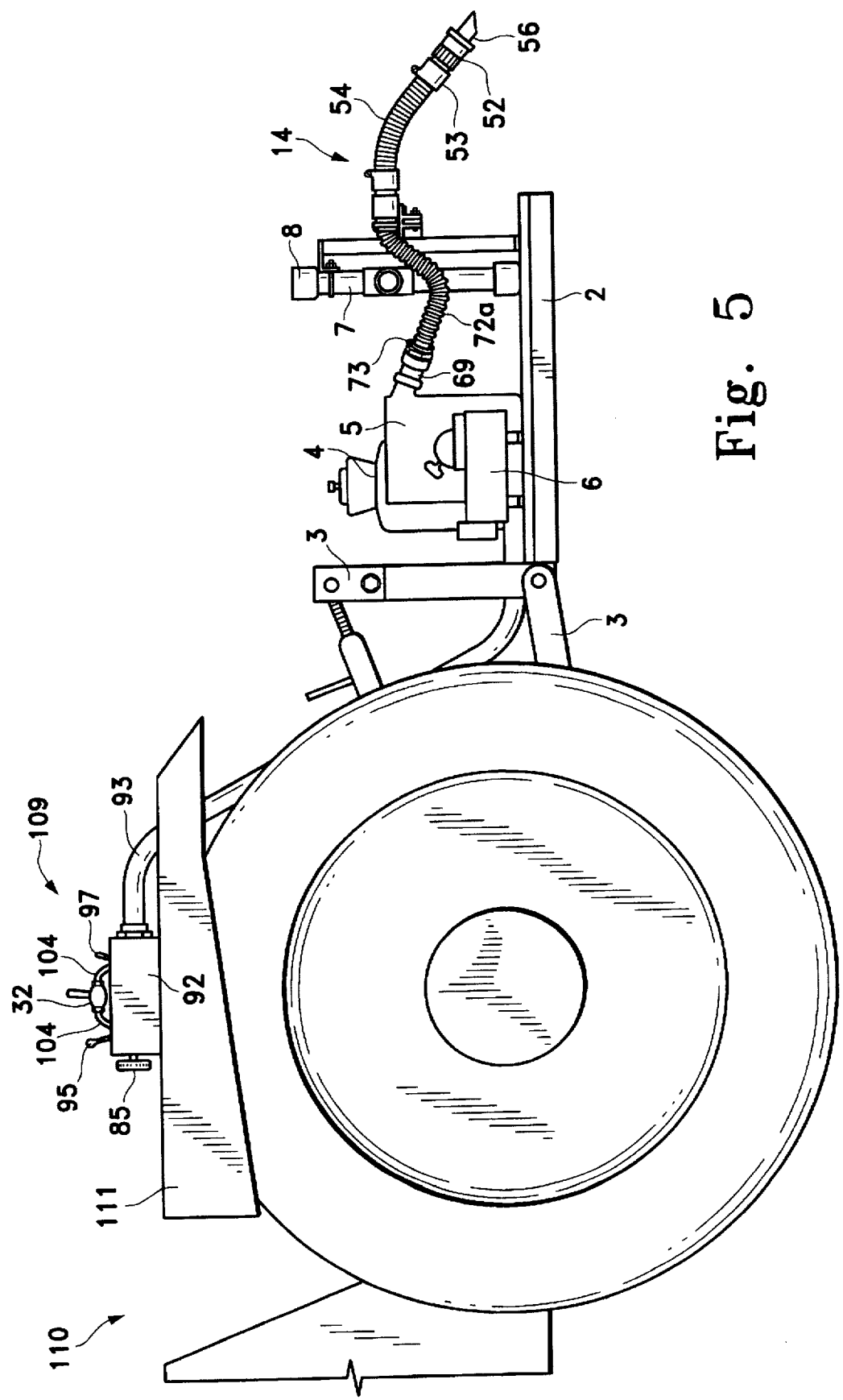

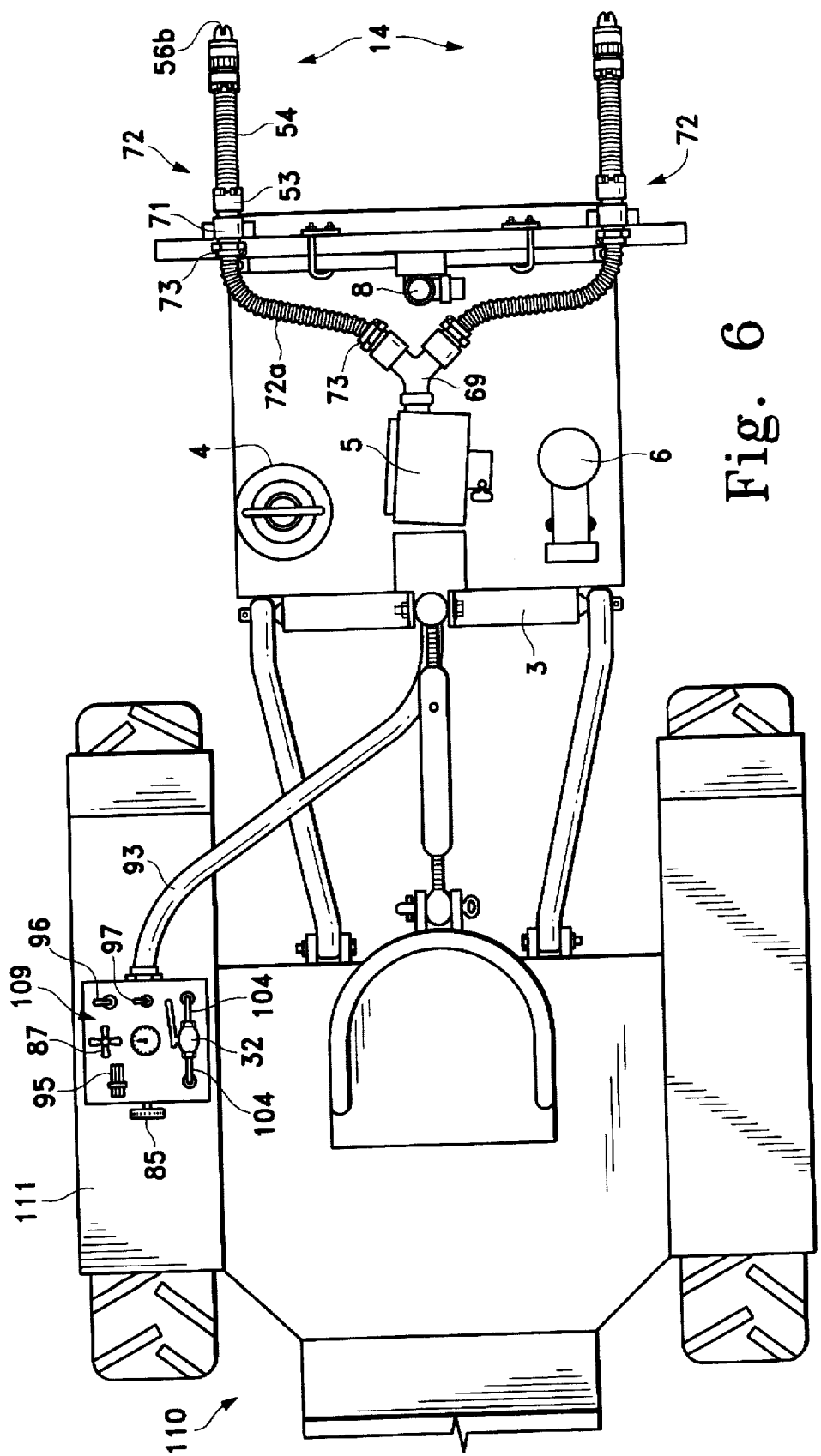

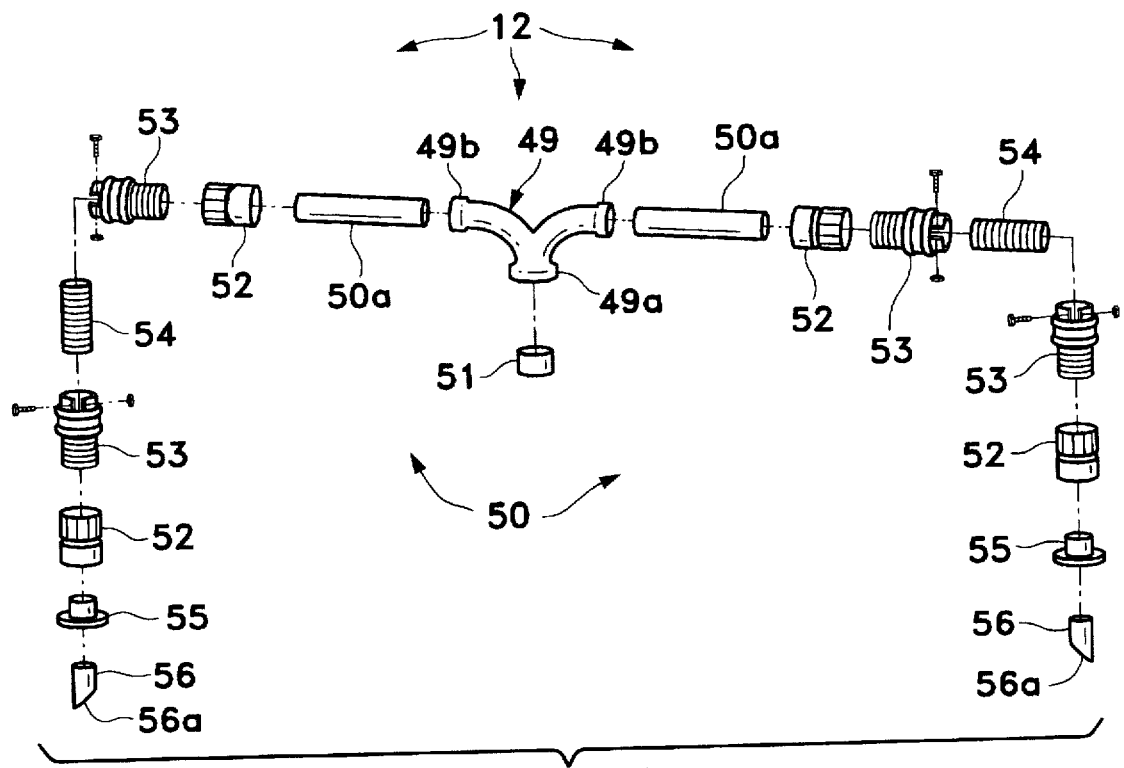
Fig. 7a
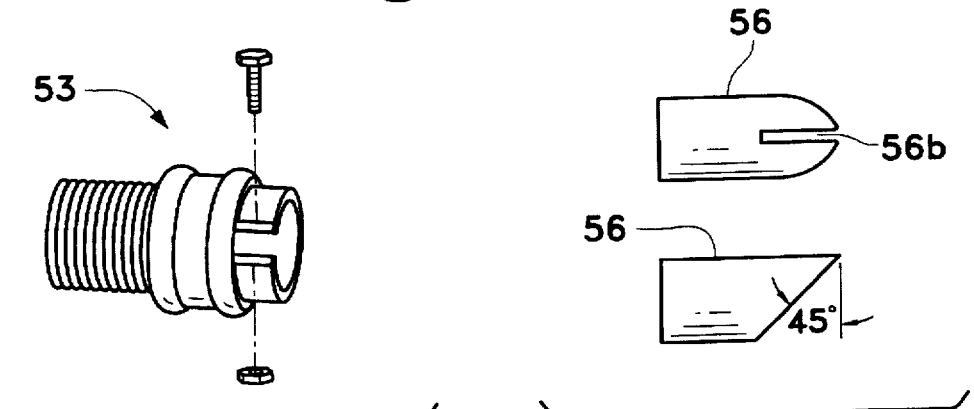
Fig. 7b
Fig. 7d
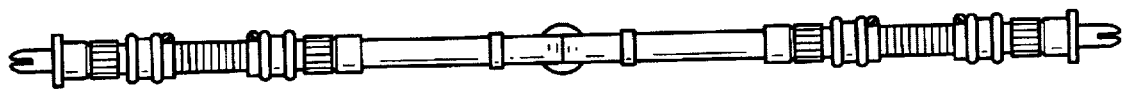
Fig. 7c

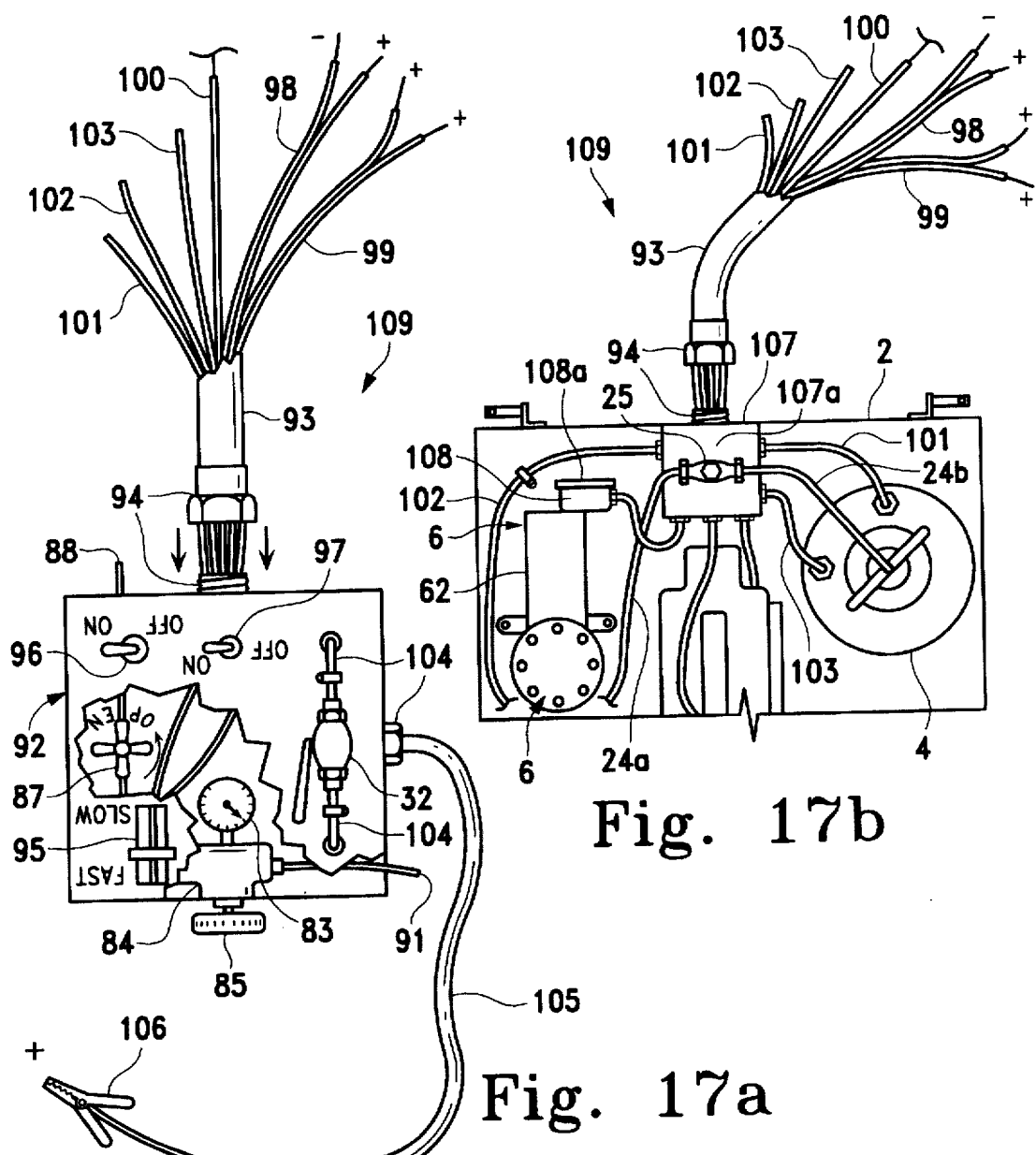
Fig. 17a
Fig. 17b
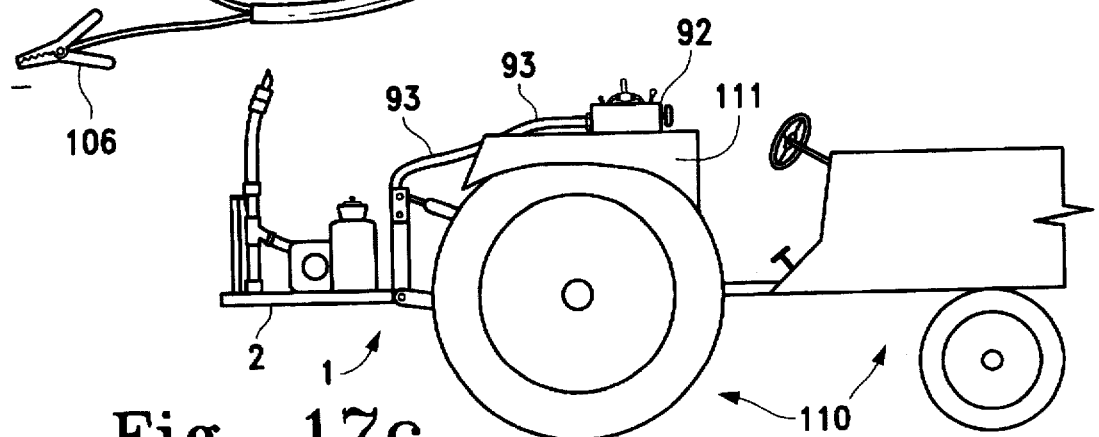
Fig. 17c

BENEFICIAL INSECT EGG SPRAYING DEVICE

FIELD OF THE INVENTION

This invention relates to a device for spraying beneficial insect eggs onto agricultural commodities. The eggs are in an adhesive composition which allows them to adhere to plants.

BACKGROUND OF THE INVENTION

Chemical insecticides are used to control insects that damage agricultural commodities such as grapes, cotton, barley, citrus, pecans, Christmas trees, etc. However, recent concerns about insecticide residues on commodities, resistance of insects to chemical insecticides, hazardous exposure to pesticide applicators, environmental contamination, destruction of natural biocontrol agents, such as beneficial insects, and lack of newly developed insecticides have increased the need for alternative control methods. Furthermore, as pests become more resistant to pesticides, more frequent treatments are required which increases the human health hazard.

An alternative to chemical pesticides is the use of biocontrol agents such as beneficial or predaceous insects which eat harmful insects. To date, there is no practical or adequate way to deliver known quantities of predaceous insects to pest infested plants. Eggs are usually applied to plants by shaking them from a container onto the plant foliage. A large percent of the eggs fall to the ground and are quickly destroyed by ants and other predators.

Larvae that emerge from the fallen eggs which escape predators are usually unable to find their way back up the plant and starve to death and the infesting insect on the plant continues to do damage. Some lacewing producers sell larvae from hatched eggs which are then shaken onto plants. However, this too is very inefficient since lacewings are cannibalistic, and when confined to a container consume each other. Furthermore, when larvae are shaken onto plants, like the unhatched eggs, most of the larvae fall to the ground and are destroyed by ants or starve to death.

U.S. patent application Ser. No. 08/175,058, now U.S. Pat. No. 5,484,504 issued Jan. 16, 1996, (Tedders et al) discloses devices for attaching beneficial insect eggs using a non-toxic adhesive to string and delivering the egg-containing string to plants. However, these devices do not spray the eggs in a non-toxic adhesive directly onto plants.

One prior art method (Dreistadt et al, Entomophaga, Volume 31(4), pp. 397–400, 1986), discloses the use paper strips with thin lines of rubber cement for attaching lacewing eggs for placement in trees. The paper tapes are prepared manually and attached to trees manually. The disclosed process takes several days since the rubber cement has to dry for several days prior to attachment of the eggs in order to eliminate toxic solvents. Upon hatching, larvae tend to become entangled by the tacky rubber cement and die. There are various types of prior art devices for attaching and delivering beneficial insect eggs to agricultural commodities. For example, U.S. Pat. No. 3,847,113 ('113) discloses a device which pastes insect eggs on a substratum. The '113 device is not designed for field use and requires several additional labor intensive acts. Eggs of a host insect are applied in a single layer to paper and excess eggs are vibrated or scraped off. The layer of host insect eggs on paper is then exposed to a parasitic wasp such as Trichogramma spp. in a separate cage where the eggs are parasitized by the Trichogramma. The excess eggs, which would have been vibrated or scraped off, would necessarily have to be manually recycled into egg loading bin 1 of '113. In order to apply eggs of other beneficial insects, such as lacewing eggs which are 25 times larger than the host egg used in '113, it would be necessary to use large amounts of filler in order to distribute only a few eggs onto the glued surface in order to prevent cannibalism once the eggs hatch. Furthermore, the device disclosed in '113 does not separate the paper with eggs into narrow strips which could be distributed over long distances but instead separates the paper into squares that are manually attached to plants. If long lengths of narrow paper were prepared, it would require manual preparation of the strips and some method of attachment to plants at frequent intervals. In transporting tape paper with eggs to the field and in applying them to plants several problems must be dealt with, such as the wind, overheating of eggs in the carrying container, injury and dislodgement of eggs when large volumes are transported in containers, and the requirement of intensive labor for applying individual strips at each site or to each plant. Finally, the '113 device only operates at one speed and is regulated by the slit size in the bottom of egg bin 1 and by vibrator 3.

U.S. Pat. No. 4,260,108 discloses a device for airborne release and broadcast of loose insect eggs. The disadvantages of this technique are similar to the disadvantages of the manual distribution of eggs discussed above i.e., the eggs do not necessarily fall onto the plants.

There are devices for ultra low-volume application of liquid and particulate insecticides. However, in ultra low-volume spraying, the orifice size of the nozzles would crush living insect eggs. U.S. Pat. No. 3,900,165 discloses a hand-carried low-volume spraying apparatus for delivery of insecticides. It includes a gasoline engine, centrifugal compressor, a spraying head, and a bottle to contain the insecticide solution. The pressurized air and insecticide are mixed in the sprayer head just prior to discharging the insecticide out of the sprayer passages in droplets ranging in size of from about 5–15 microns in diameter. The insecticide containing bottle is remote from the pressurizing means. This apparatus is only useful for spraying solutions and not suspensions such as an aqueous carrier contain beneficial insect eggs since there is nothing to keep the eggs from settling out of the suspension. Furthermore, the forces created in the mixing chamber in the nozzle as well as in the passage through the air vortex would be damaging to the beneficial insect eggs.

U.S. Pat. No. 4,026,469 ('469) discloses an apparatus for low volume spraying of bushes and trees. The apparatus propels pressurized air out of nozzles. The air oscillates and causes the leaves to move back and forth so that an emulsion spray from separate nozzles entirely coats the leaves both in the interior and exterior of the tree's canopy. The emulsion is directed into the blast of pressurized air in order to create a fine mist of emulsion. The apparatus includes a centrifugal compressor driven by an external power source, a spray tank, headers for spraying the emulsion, and nozzles for providing a nutating blast of air. However, the orifice size of the nozzles would crush insect eggs, the emulsion passing through the pump would crush insect eggs, and insect eggs would be smashed against the sides of the nutation flaps.

U.S. Pat. No. 5,269,461 ('461) discloses a system for dispensing small, ultra low-volume droplets of liquid or solid particles that includes a gasoline engine, a class III centrifugal fan, a compressor, a fuel tank and a battery. The sprayer includes a nozzle assembly that is elevated with the discharge end in a generally horizontal position. The nozzle assembly includes, at the discharge end, four liquid atomizing nozzles equally spaced axially downstream of the main airstream nozzle. There are openings arranged concentrically about the outer peripheral surface of the airstream nozzle which allows secondary airflow which forms a protective sleeve of air about the primary airstream. As with the ultra low-volume sprayers, the eggs would be crushed by the nozzle size and by the centrifugal blower fan blades.

While various devices have been developed for the delivery of beneficial insect eggs to agricultural commodities, there still remains a need in the art for a more effective device for economically applying large quantities of predaceous insects, with equal distribution, to pest infested plants. Furthermore, various spraying devices have been developed for the delivery of chemical solutions and emulsions, however, there is no spray device available that will not injure insect eggs or deliver and evenly distribute beneficial insect eggs with a non-toxic glue to infested plants. The development of reasonable and workable delivery systems for beneficial insect eggs is paramount to the development of biocontrol in agriculture.

The present invention provides a simple, cost effective, alternative strategy for delivering known quantities of any predaceous insect which is different from the prior art devices and solves some of the problems associated with the prior art devices.

SUMMARY OF THE INVENTION

It is therefore, an object of the present invention to provide a device for spraying aqueous solutions containing eggs of beneficial insects onto plants.

Another object of the present invention is to provide a low volume spray device for spraying aqueous solutions containing eggs of beneficial insects onto plants.

A further object of the present invention is to provide a device for spraying aqueous solutions containing eggs of beneficial insects and nontoxic adhesives onto plants.

A still further object of the present invention is to provide a device with a back pressure regulator system for spraying aqueous solutions containing eggs of beneficial insects onto agricultural commodities.

It is also an object of the present invention to provide a method for spraying eggs of beneficial insects onto agricultural commodities.

Further objects and advantages of the present invention will become apparent from the following description.

BRIEF DESCRIPTION OF THE DRAWINGS

FIG. 5 is a side view of ESD 1 with air system 14 for spraying row crops with beneficial insects.

FIG. 6 is a top view of ESD 1 with air system 14 for spraying row crops with beneficial insects.

FIG. 7a is a perspective exploded view of air system 12 for spraying moderate height plants with beneficial insect eggs.

FIG. 7b is an enlarged view of Greenfield, squeeze type, flex/box connector 53.

FIG. 7c is a top view of the assembled spray arms 50.

FIG. 7d is an enlarged top and side view of formed outlet 56.

FIG. 12b is a perspective exploded view of slide bar assembly 79 that fits on either end of strut system channel 77 seen in FIG. 12a.

FIG. 17a is a view of remote control assembly 109.

FIG. 17b is a top view of ESD 1 on deck and framework 2 showing electrical conduit 93 which connects wires and tubing of ESD 1 to remote control assembly 109 that sits on tractor fender 111.

FIG. 17c is a side view of ESD 1 on deck and framework 2 hitched to tractor 110 with remote control assembly 109 attached to fender 111.

DETAILED DESCRIPTION OF THE INVENTION

Figure 1:
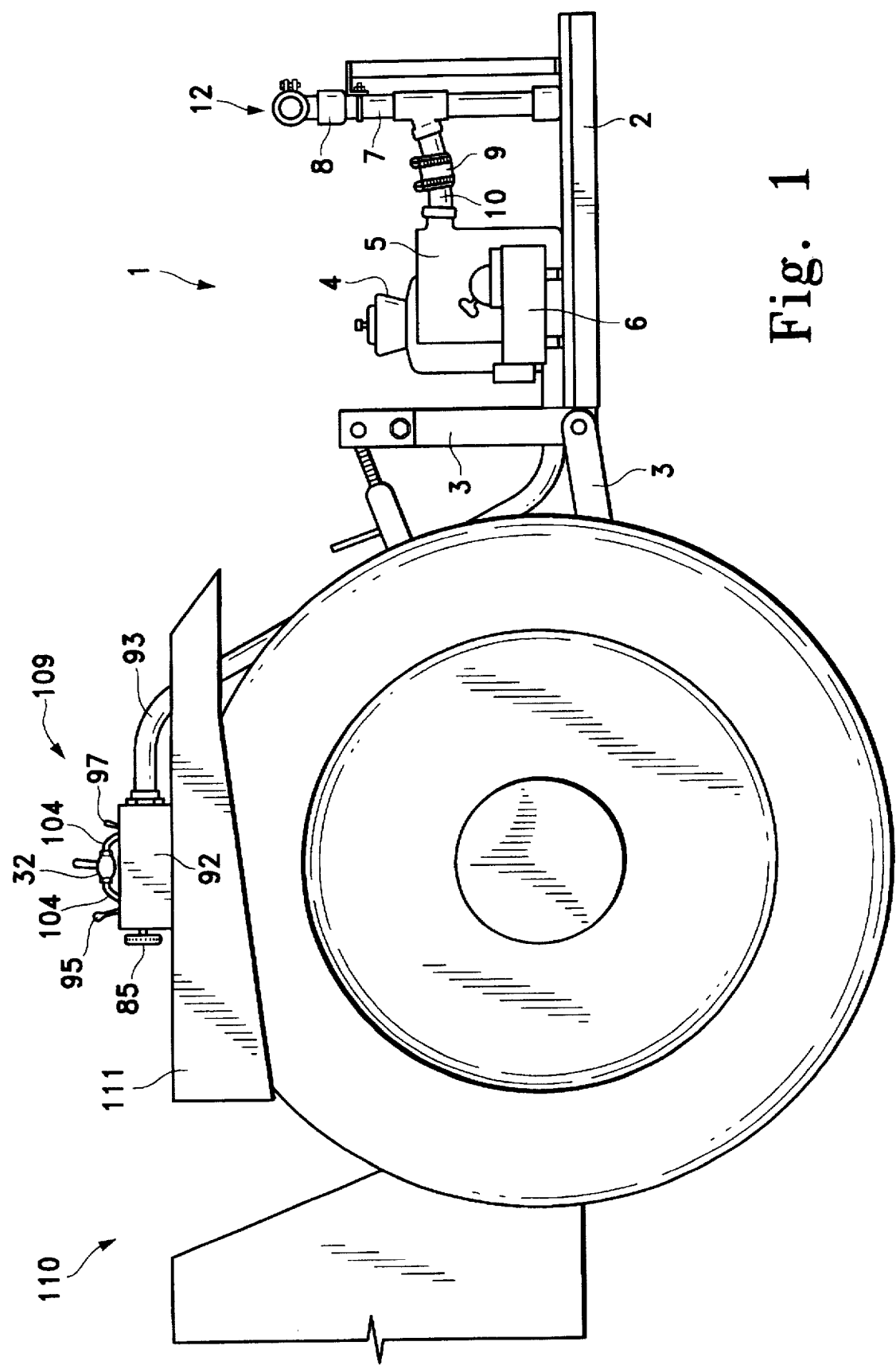
FIG. 1 is a side view of ESD 1 with air system 12 for spraying moderate height plants with beneficial insects.
Figure 2:
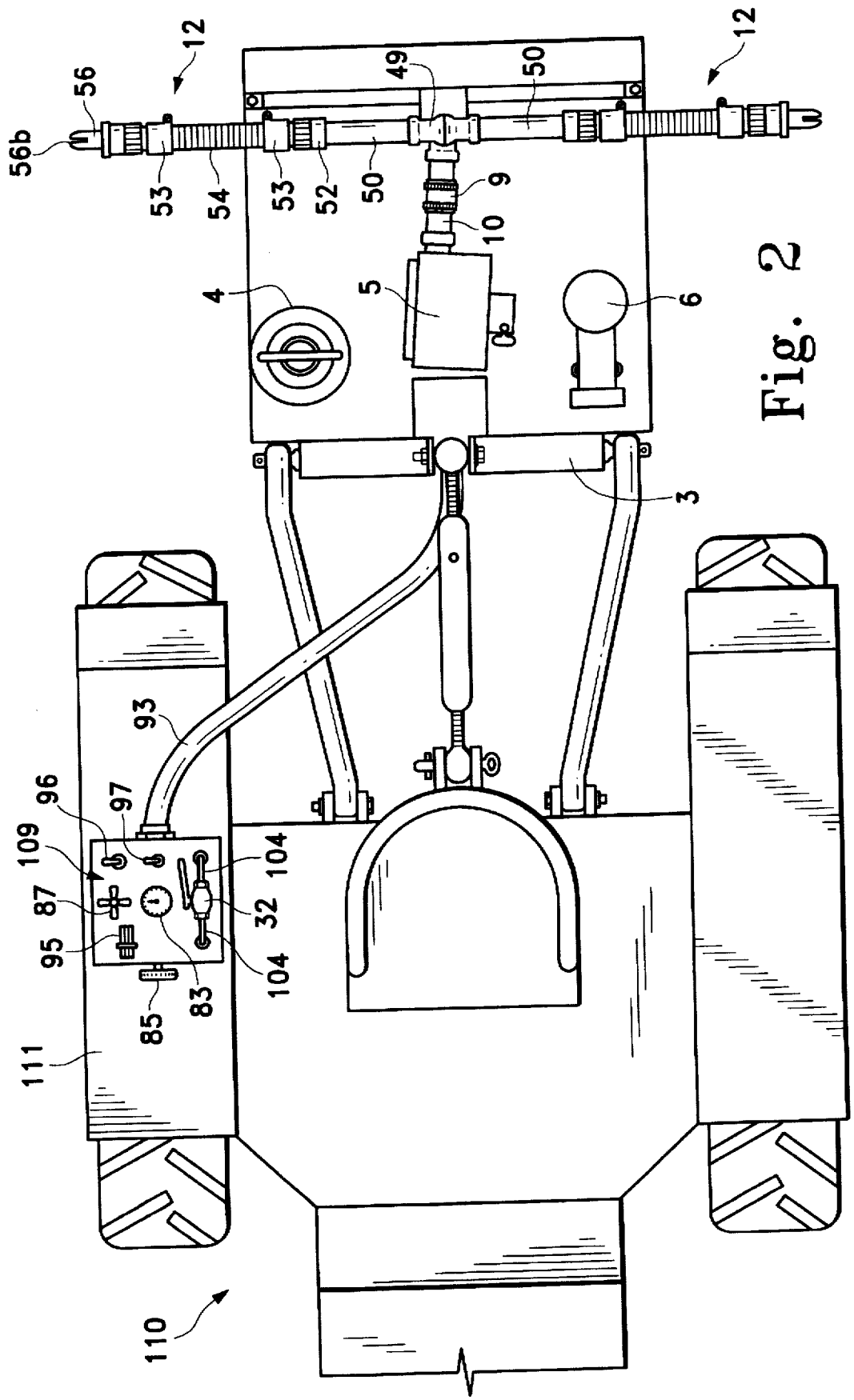
FIG. 2 is a top view of ESD 1 with air system 12 for spraying moderate height plants with beneficial insects.
Figure 3:
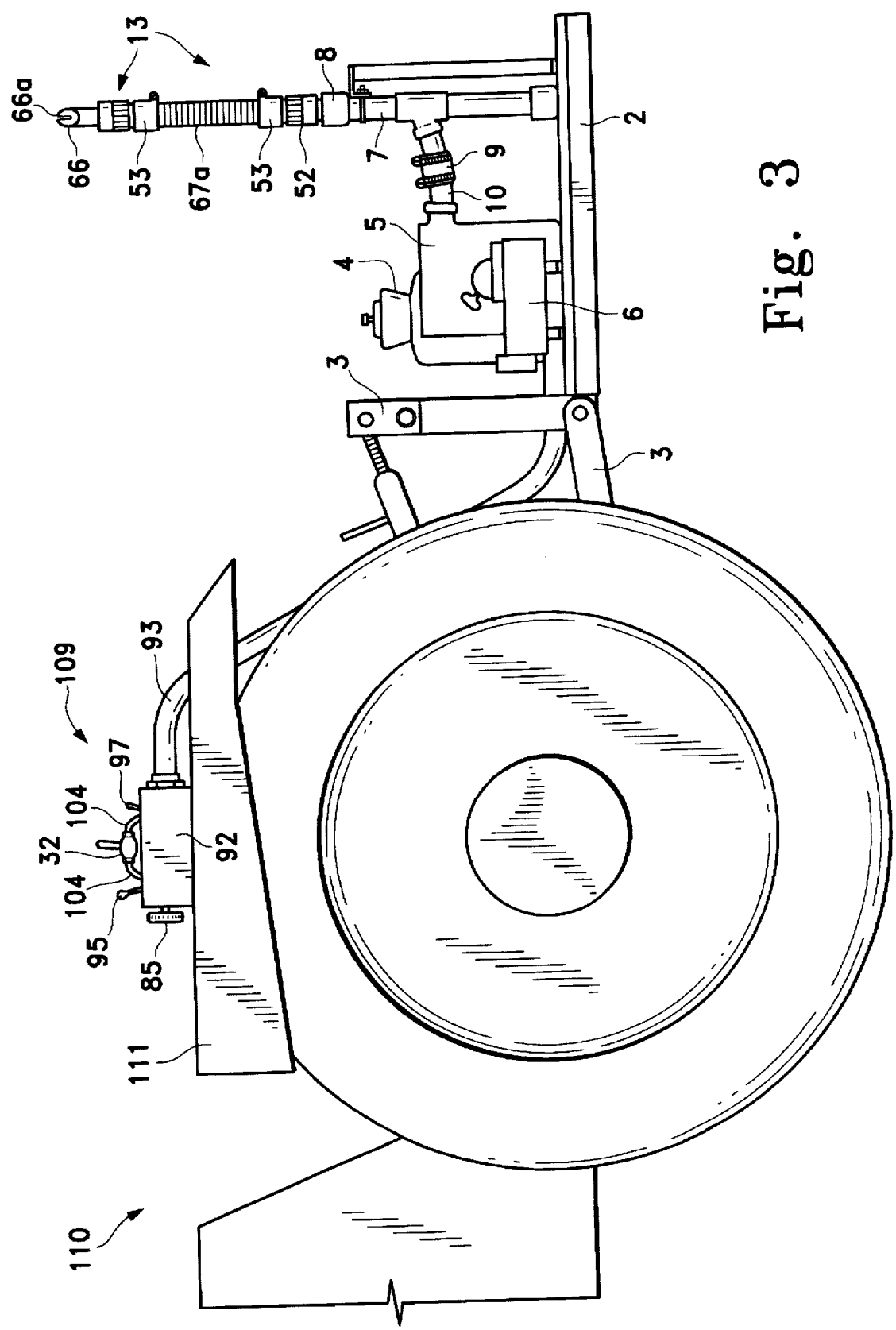
FIG. 3 is a side view of ESD 1 with air system 13 for spraying trees with beneficial insects.
Figure 4:
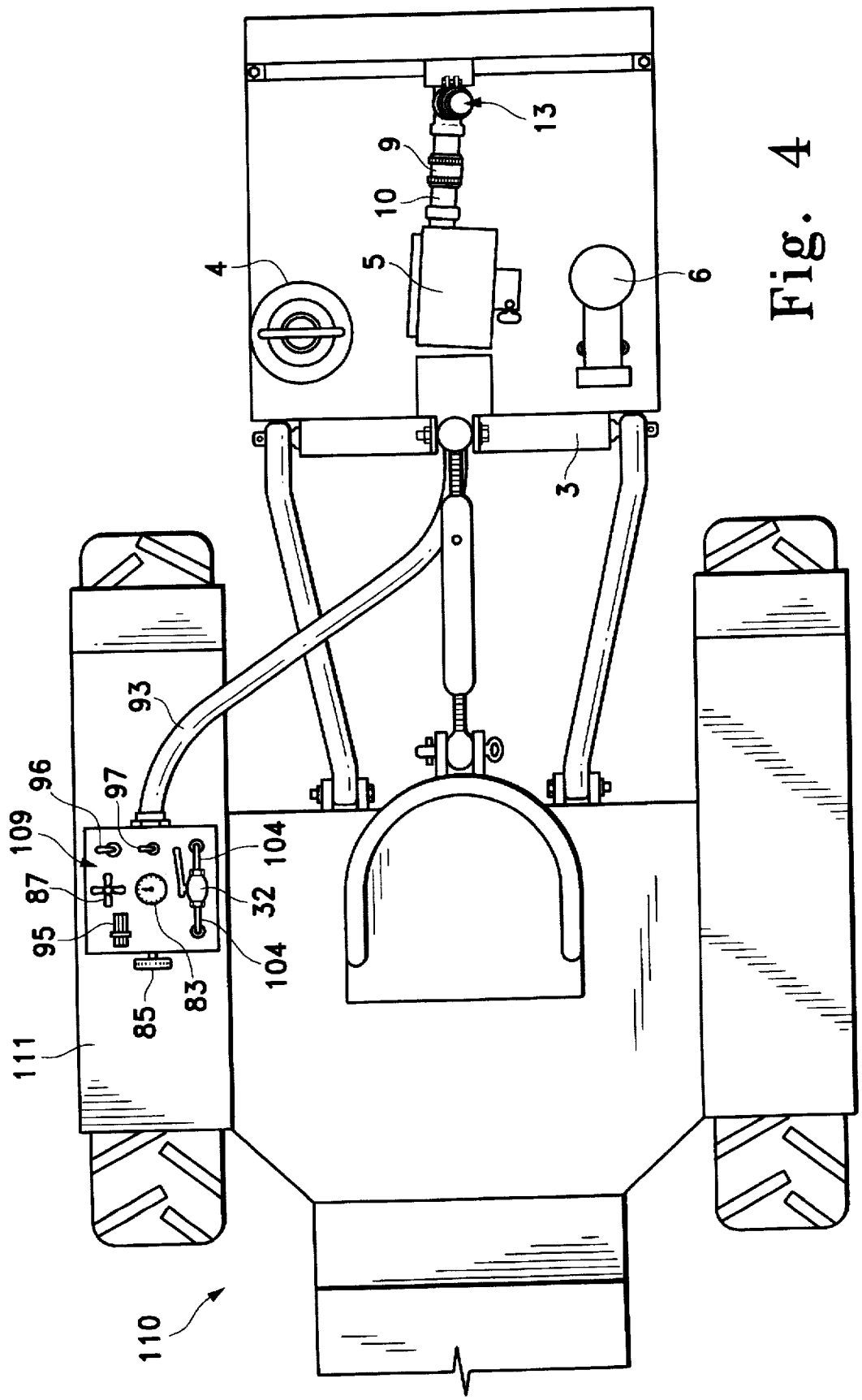
FIG. 4 is a top view of ESD 1 with air system 13 for spraying trees with beneficial insects.

Beneficial insect egg spraying devices (ESDs) 1 incorporating the features of the present invention are illustrated in FIGS. 1–6. ESD 1 is made up of one of several air systems 12, 13, or 14 (FIGS. 7a–d–11), a pressure release system 15, one of two aqueous solution assemblies 16 or 17, a compressed air system 18, a tank assembly 11, and a remote control assembly 109. ESD 1 is mounted on a deck 2 supported by a tractor 3-point hitch 13 with part of the remote control assembly 109 mounted on tractor fender 111.

Figures 8A, 8B:
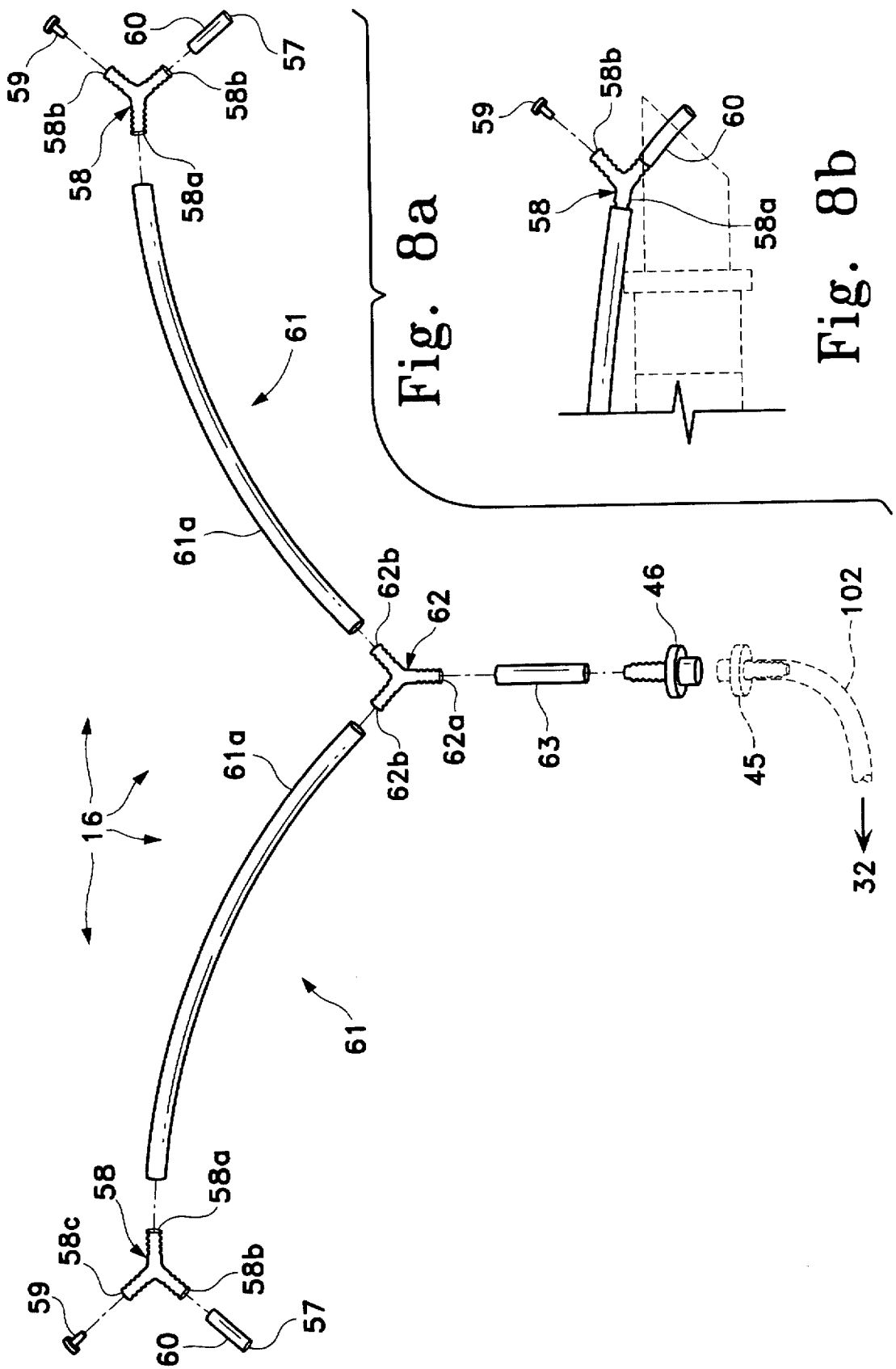
FIG. 8a is a perspective exploded view of aqueous solution system 16 for spraying moderate height plants and row crops with beneficial insects.
FIG. 8b is an enlarged side view of plastic Y-fitting 58 showing how it attaches to tubing 61a and formed outlet 56.
Figure 13B:
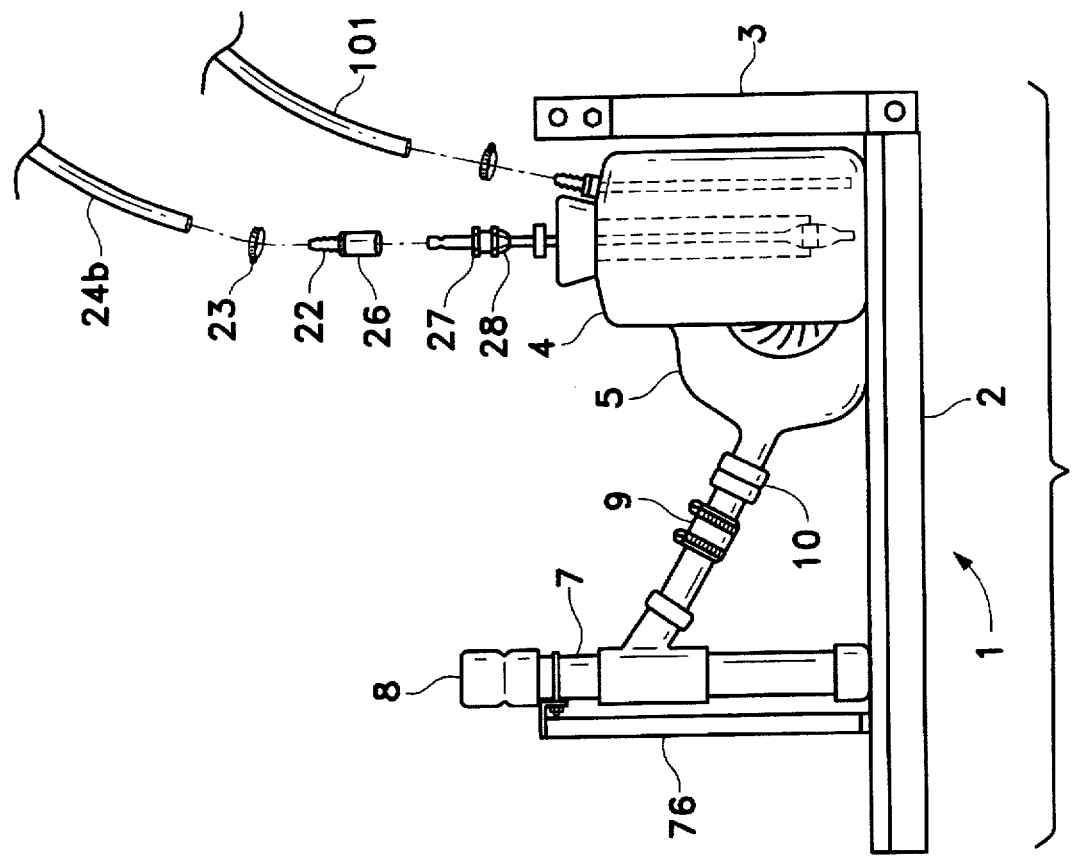
FIG. 13b is a perspective side view of ESD 1 mounted on deck and framework 2.
Figure 13A:
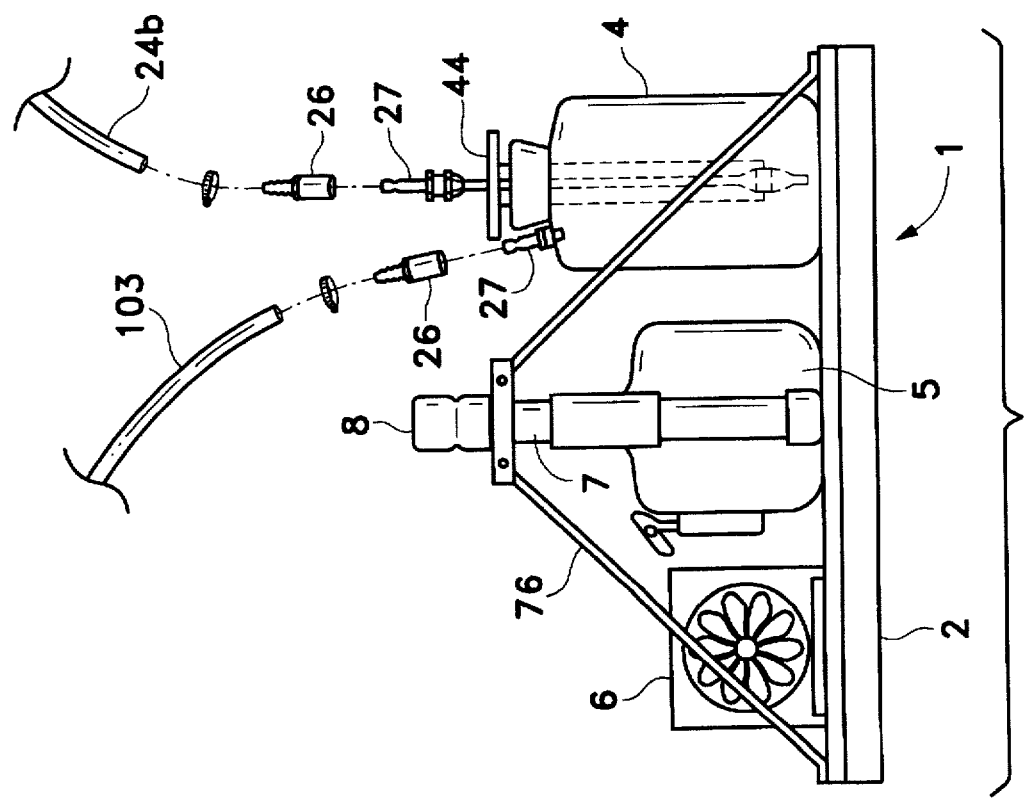
FIG. 13a is a perspective back view of ESD 1 mounted on deck and framework 2.

The first embodiment has an air system 12 (FIGS. 7a–7d) useful for spraying beneficial insect eggs onto plants of moderate height such as grapes, hedge rows, shrubs, etc. The air system 12 has two spraying arms 50, 180° apart, connected by a 2" PVC drain tee 49 (see FIG. 7a–d). Tee 49, with a 2" length of 2" ID PVC pipe 51 connected at the inner end 49a of tee 49, connects air system 12 to gasoline engine driven blower fan 5 (Echo®, Echo, Inc., 400 Lakewood Road, Lake Zurich, Ill. 60047) (FIG. 13b) through a vertical 2" PVC stand pipe 7 with a 2" receiving coupling 8 (FIGS. 13a and 13b). Each arm 50 is made up of a series of pipes and connectors either glued or threaded together. For each arm 50, glued to the outer end 49b of tee 49 is an 8" length of 2" ID PVC pipe 50a. Glue-fitted to the outer end of pipe 50a is a 2" ID PVC female adaptor 52. Threaded into the outer end of adaptor 52 is a 2" greenfield squeezetype flex/box connector 53 (FIGS. 7a and 7b). A 10¾" length of 2" flexible exhaust pipe 54 is connected to connector 53. On the outer end of pipe 54 is a second greenfield squeezetype flex/box connector 53. A second 2" PVC female adaptor 52 is threaded on to connector 53. Glue-fitted to the end of adaptor 52 is a 2"—1½" reducer bushing 55. Glued to the 1½" end (outer end) of bushing 55 is a 3½" length of 1½" ID PVC pipe 56 with the outer end cut at a 45° angle to form air outlet port 56a (FIG. 7d). Pipe 56 has a ¼"×1⅛" longitudinal slot 56b cut into its top to receive aqueous solution outlet port 57 (FIG. 8a–b). The total length of each spray arm 50 is approximately about 27¼" (FIG. 7C).

Figure 16:
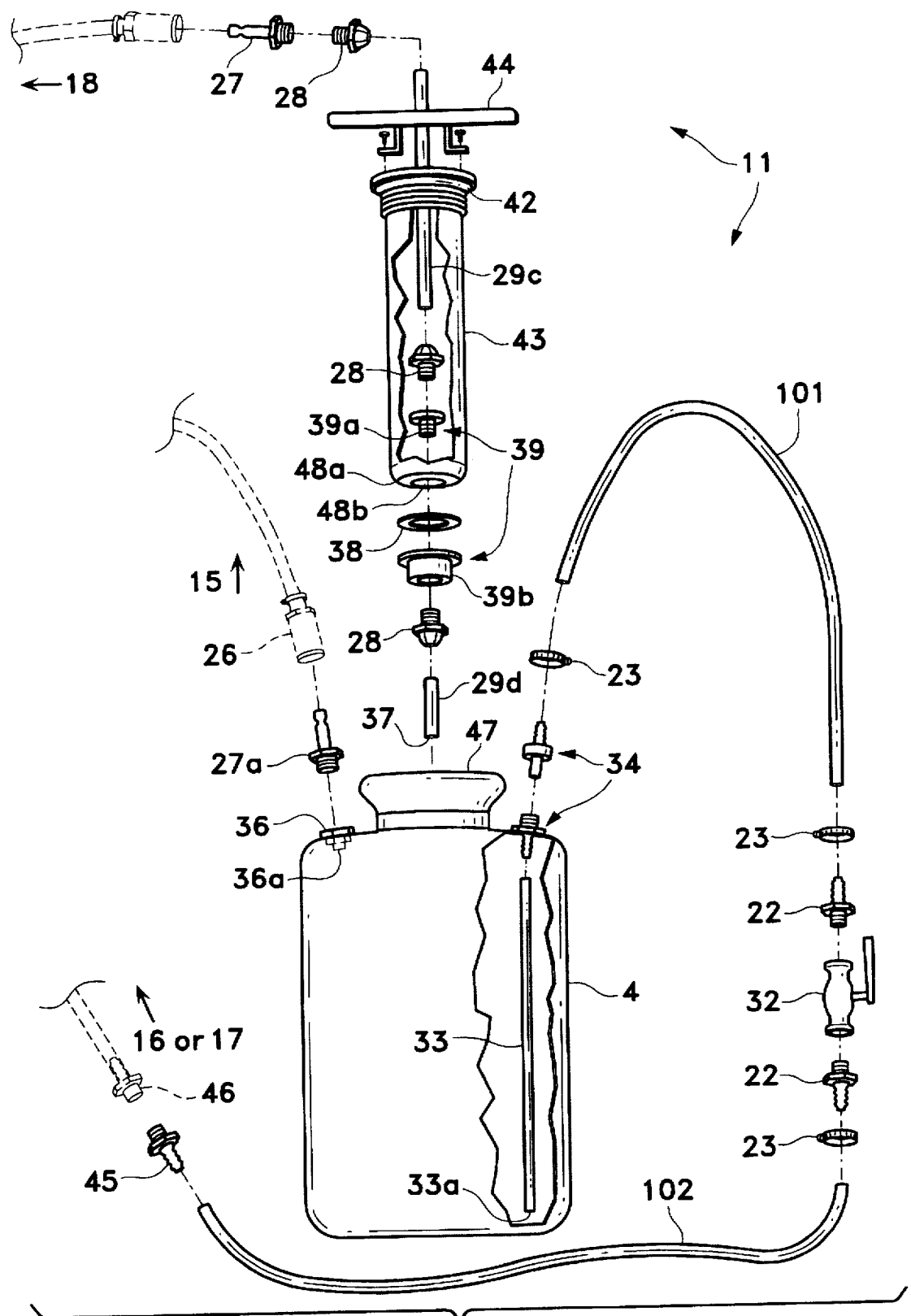
FIG. 16 is a perspective exploded view of tank assembly 11 showing the connections to compressed air system 18, pressure release system 15, and air systems 12, 13, or 14.

Aqueous solution assembly 16 is connected to spray arms 50 of air system 12 and to spray tank 4 through ¼" brass ball valve 32 (flow valve) (see FIGS. 8a–b and 16) of tank assembly 11. Assembly 16, like air system 12, has two arms 61, 180° apart, connected by an 8 mm plastic barbed Y-fitting 62. The inlet port 62a of fitting 62 is connected with a 2½" length of ³⁄₁₆" ID TYGON™ tubing 63, attached to ¼" brass ball valve 32 through tubing 102 attached to a male ³⁄₁₆" plastic union 45 connected to a female ³⁄₁₆" plastic union 46. Tubing 63 attaches to the barbed end of female union 46. Each arm 61 is made up of tubing and a Y-fitting. A 30" length of ⅛" ID TYGON™ tubing 61a is attached to one of outlets 62b of Y-fitting 62 and to 6 mm plastic barbed Y-fitting 58 at inlet 58a (FIG. 8b). A one-inch length of ³⁄₃₂" ID TYGON™ tubing 60 is stretched over the end of one of the outlet ports 58b of fitting 58. The other port 58b is sealed with threaded plug 59 screwed into the port.

The second embodiment is air system 13 (FIGS. 9a–b), useful for spraying commodities such as pecan trees, walnut trees, Christmas trees, or anything that is a tree or grows on a tree. The air system has a single spraying arm 67 which is attached to blower fan 5 through vertical 2" ID PVC stand pipe 7 with a 2" receiving coupling 8 (FIG. 13b). A 2" length of 2" ID PVC pipe 51 is inserted into coupling 8. A 2" PVC female adapter 52 attaches to the outer end of pipe 51 and a 2" greenfield squeezetype flex/box connector 53 attaches to the outer end of adaptor 52. A 12" length of 2" ID flexible exhaust pipe 67a is attached to the outer end of connector 53 and a second greenfield squeezetype flex/box connector 53 is attached to the outer end of pipe 67a. Second connector 53 is threaded onto a second 2" PVC female adaptor 52 which has a 5" length of 2" ID PVC pipe 66 glued to adaptor's 52 outer end. Pipe 66 is cut at a 45° angle to form air outlet port 66b. A ¼"×1⅛" longitudinal slot 66a is cut into the longest side of the top of pipe 66. Slot 66a receives tubing 60 of aqueous solution assembly 17 (FIG. 10).

Figures 9A, 9B:
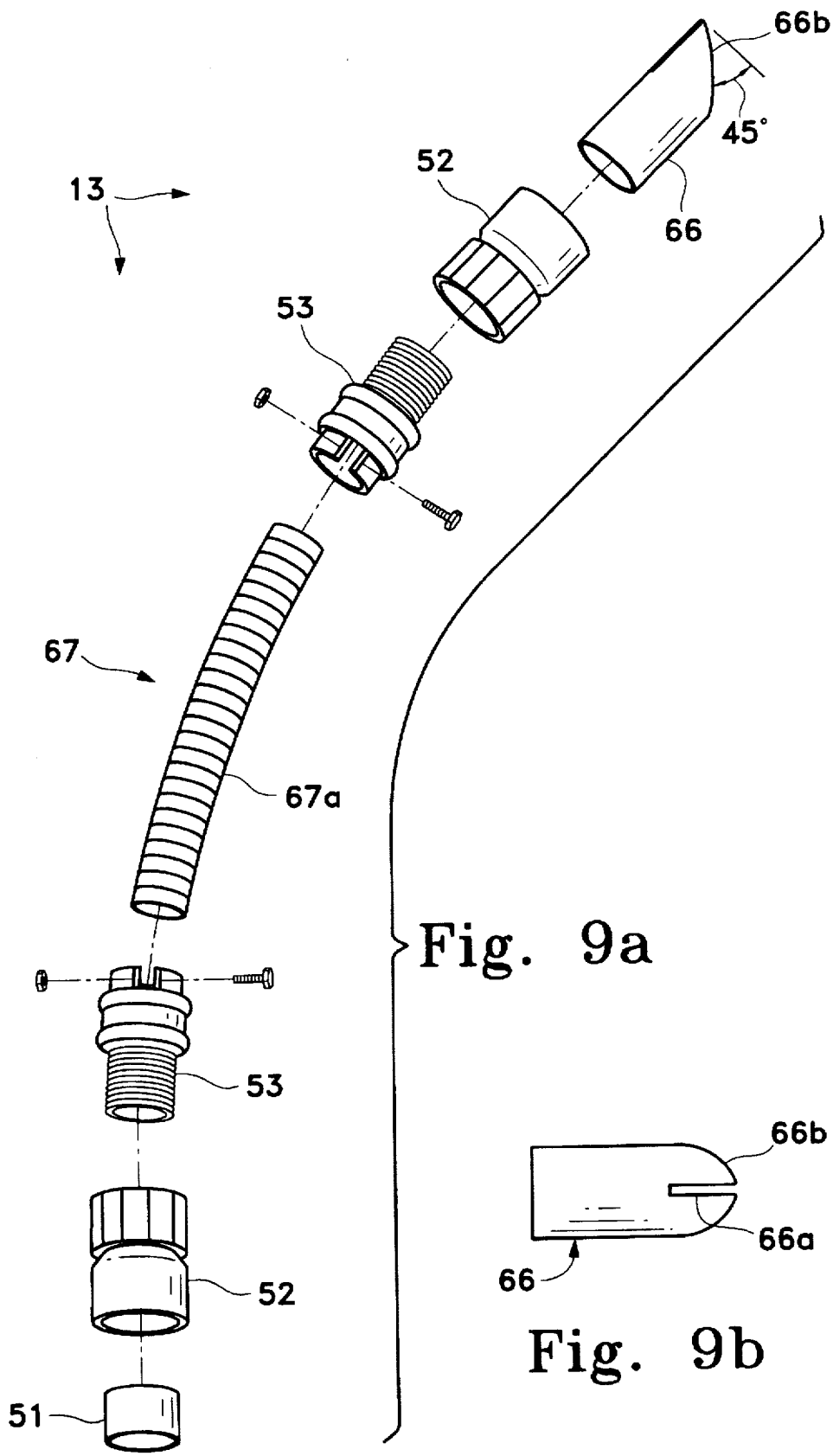
FIG. 9a is a perspective exploded view of air system 13 for spraying trees with beneficial insects.
FIG. 9b is an enlarged view of formed air outlet 66 showing longitudinal slot 66a and air outlet port 66b.
Figure 10:
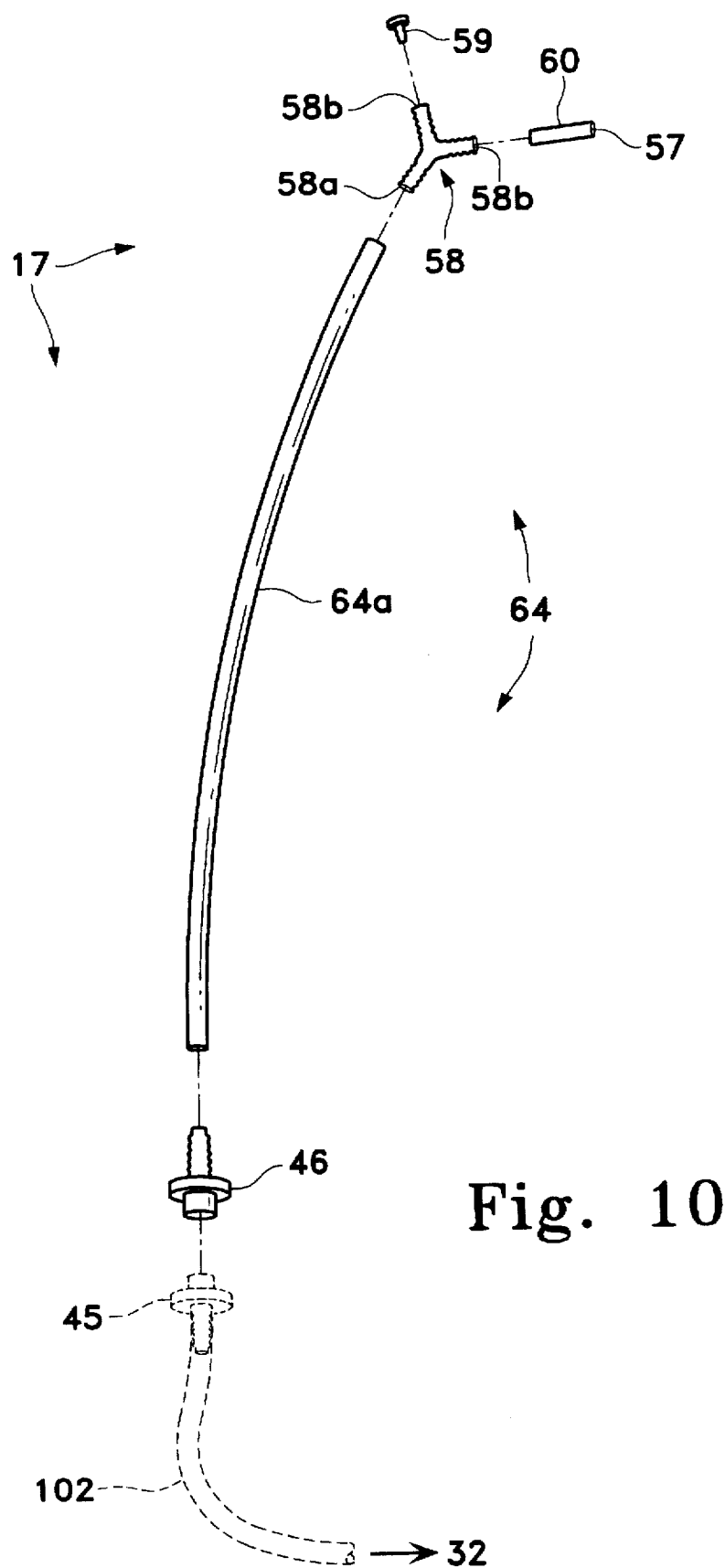
FIG. 10 is a perspective exploded view of aqueous solution system 17 for spraying trees with beneficial insects.
Figures 11A, 11B:
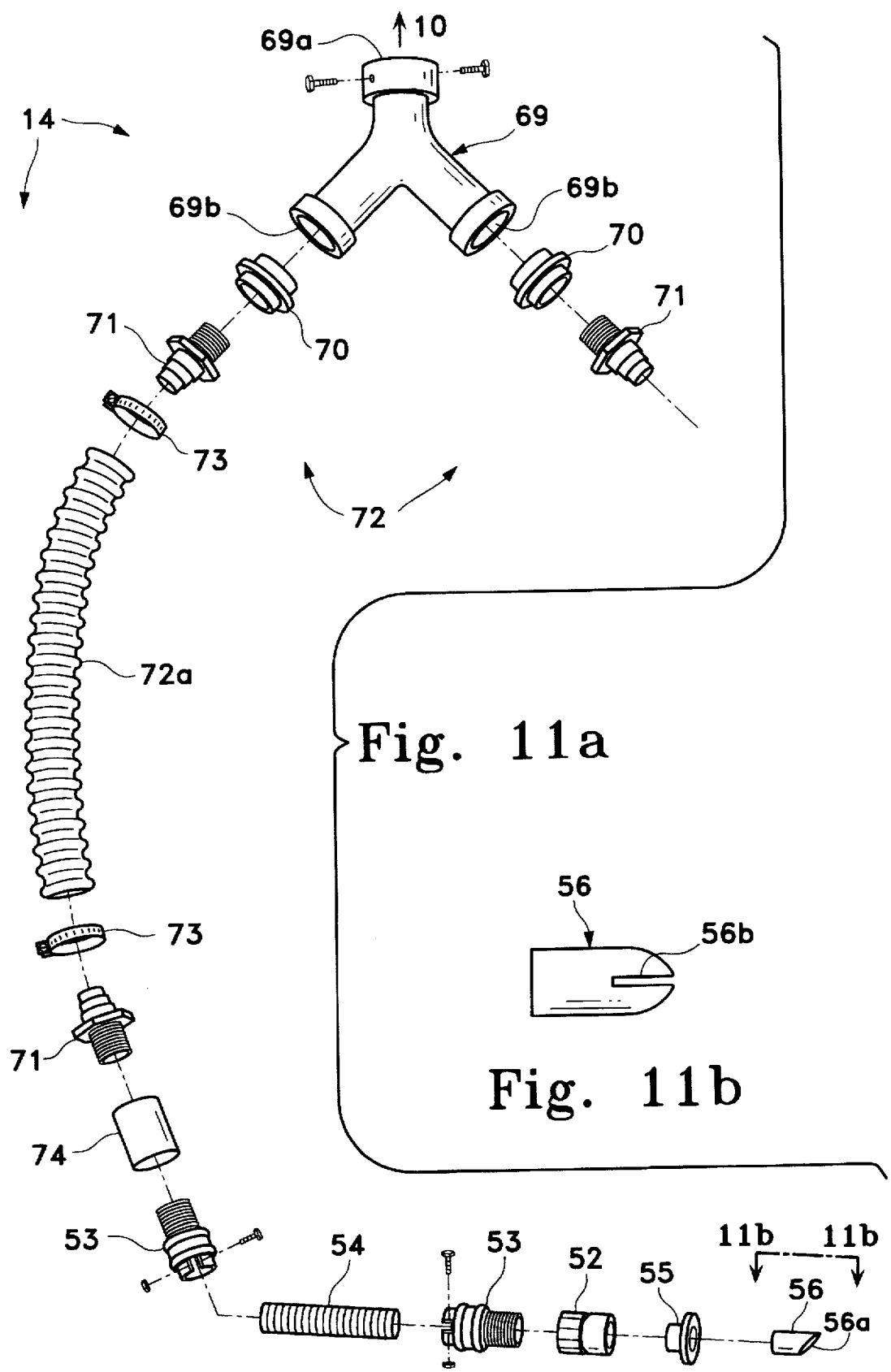
FIG. 11a is a perspective exploded view of air system 14 for spraying row crops with beneficial insects.
FIG. 11b is an enlarged view of formed air outlet 56 showing longitudinal slot 56b.

Aqueous solution assembly 17 is connected to spray arm 67 and to spray tank 4 through ¼" brass ball valve 32 of tank assembly 11 through ³⁄₁₆" male plastic union 45 as described above for the first embodiment of the air system (FIG. 10). Assembly 17 is a single arm 64 connected to a ³⁄₁₆" female plastic union 46. A 21" length of ⅛" ID TYGON™ tubing 64a attaches to the barbed end of union 46 and the outer end of tubing 64a attaches to a 6 mm plastic barbed Y-fitting 58 at inlet port 58a. As in the first embodiment, a 1" length of ³⁄₃₂" ID TYGON™ tubing 60 is stretched over the end of one of outlet ports 58b of fitting 58. The other port 58b is sealed with threaded plug 59 screwed into the port. The outer end of tubing 60 forms aqueous solution outlet port 57. Tubing 60 inserts into the slot 66a of pipe 66 of air supply system 13 (FIGS. 9a–b).

Figure 12A:
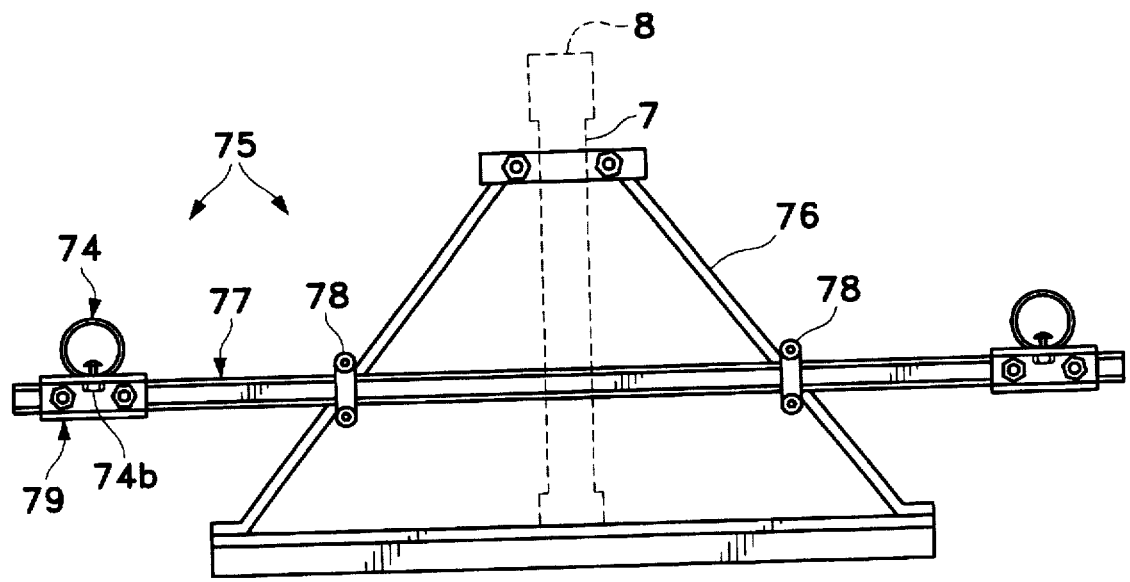
FIG. 12a is a perspective view of the mounting assembly 75 for air system 14 with aqueous solution system 16.
Figure 12B:
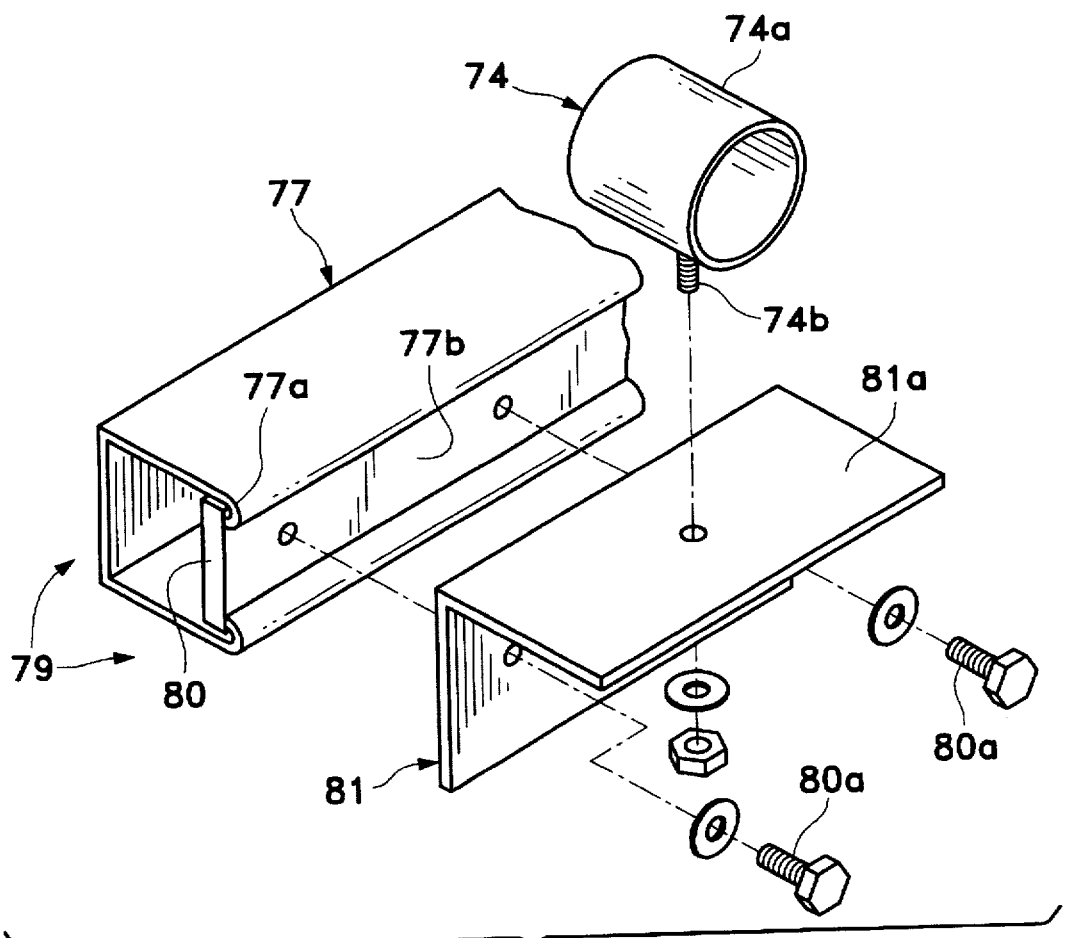

The third embodiment is air system 14 and, like system 12, has two spraying arms 72 (FIGS. 11a–b) useful for spraying row crops such as cotton, beans, peas, tomatoes, beets, lettuce, broccoli, strawberries etc. Air system 14 requires an alteration in the air supply assembly at the source of the air, blower fan 5 (see FIG. 13b). A 2" PVC coupling/blower connector 10, fastened to the housing of blower fan 5 by two sheet metal screws, is removed by loosening the hose clamps on rubber coupling 9, sliding the coupling towards blower fan 5, and rotating stand pipe 7 90° clockwise. Coupling/connector 10 is removed and replaced with a 2" female PVC Y-fitting 69 where inlet end 69a is connected to blower fan 5 with the two sheet metal screws that held the 2" coupling/blower connector 10 in place. For each spraying arm 72, a 2" PVC coupling female threaded/male glue joint 70 is fitted into each of the two outlet ports 69b of the Y-fitting 69. Threaded into coupling 70, is a 2" male plastic barbed fitting 71 upon which a 31" length of 2" ID flexible plastic hose 72a is attached with a medium size hose clamp 73. At the outlet end of flexible hose 72a, a second 2" male plastic barbed fitting 71 is attached with a second hose clamp 73. A modified 2" galvanized coupling 74 connects to threaded end of barbed fitting 71. Galvanized coupling 74 is modified by drilling a ¼" hole into the center of wall 74a, passing a ¼"×1½" carriage bolt 74b through the hole perpendicular to the direction of flow of air through the coupling (FIGS. 12a and 12b). Connected to the outlet end of modified coupling 74 is a 2" greenfield squeeze-type flex/box connector 53. A 10¾" length of 2" ID flexible exhaust pipe 54 is clamped to connector 53 and the outlet end of pipe 54 is clamped to a second 2" greenfield squeeze-type flex/box connector 53. Threaded onto connector 53 is a 2" female adaptor 52 in which a 2"—1½" reducer bushing 55 is glued. Inserted into reducer bushing 55 is a 1½" ID PVC pipe 56 cut at a 45° angle on one end to form air outlet port 56a.

The modified 2" galvanized couplings 74 are fastened to mounting assembly 75 (FIGS. 12a and 12b) with ¼" carriage bolts 74b. Assembly 75 includes about a 48" length of electrical strut system channel 77, two 3"×4" U-bolts 78, and a slide bar assembly 79. Channel 77 is held in place horizontally across the rear of the sprayer by two 3"×4" U-bolts 78 which are fastened to the stand pipe brace 76. Slide bar assembly 79 is made up of a 4" length of ¼" stock aluminum bar 80, 1¼" wide, which has been drilled and tapped to receive two 1"×⅛" machine bolts 80a and is inserted on the inside of the channel, resting on lips 77a of the open side 77b of channel 77 when bolted to a 2"×2"×¼" aluminum angle 81, approximately about 4" in length, on the outside of open side 77b of channel 77, forming a sliding and locking system which allows for adjustment to widths of rows. Coupling 74 is attached to the top 81a of angle 81.

The aqueous solution assembly 16 (FIGS. 8a–b) for air system 14 (FIGS. 11a–b) is the same assembly as that used with air system 12 as described above. Aqueous solution ports 57, inserted into slot 56b of angled pipe 56 (FIG. 11b), and air outlet ports 56a, of angled pipe 56, are positioned onto mounting assembly 75 so that they face out from the rear of sprayer deck and framework 2 (not shown in FIGS. 12a and 12b). The delivered spray can be adjusted down onto the plants in the rows by bending the sections of 2" ID flexible exhaust pipe 54.

The tank assembly 11, pressure release system 15, compressed air system 18, and remote control assembly 109 are the same for each of the above air systems 12, 13, and 14 and aqueous solution systems 16 and 17.

Figure 14:
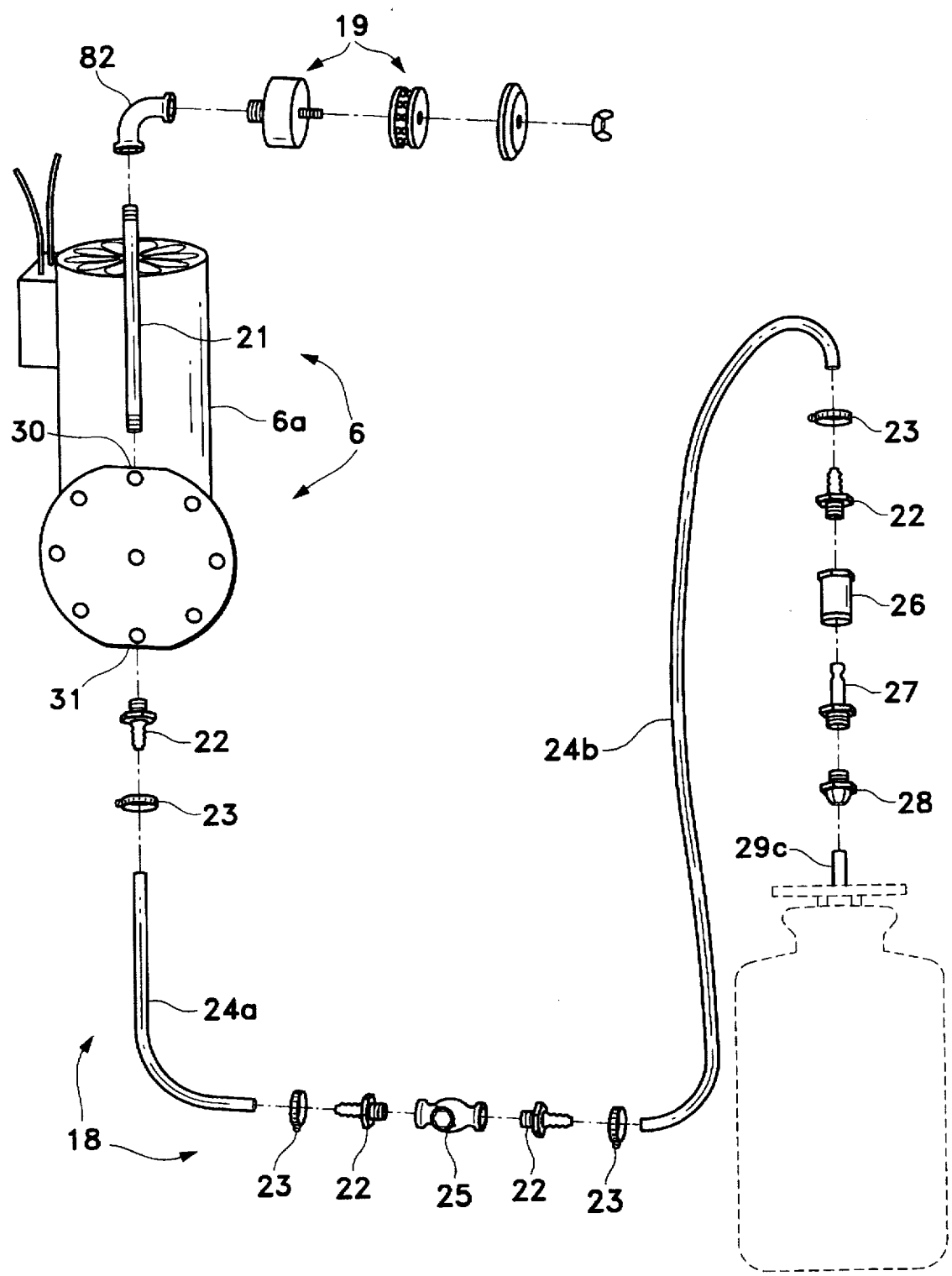
FIG. 14 is a perspective exploded view of compressed air system 18 showing its connection to spray tank 4.

Compressed air system 18 (FIG. 14) is made up of a 12 VDC Gast® diaphragm compressor 6 (¹⁄₁₆" HP, 50 PSI max. output) (Gast Manufacturing Corp., P.O. Box 97, Benton Harbor, Mich. 49023-0097), an air filter assembly 19 and a series of fittings and tubings which connects air filter assembly 19 and compressor 6 to spray tank assembly 11. A ¼" galvanized nipple 21, approximately about eight inches in length, is connected to air inlet 30 of compressor 6. A ¼" galvanized elbow 82 is threaded onto the distal end of nipple 21 and is turned up so that air filter assembly 19 is positioned perpendicular to compressor 6 (normal mounting position). Connected to air outlet 31, of compressor 6, is a ¼" male brass barbed fitting 22 with approximately 26 inches of ³⁄₁₆" ID TYGON™ tubing 24a fastened to the barbed end of fitting 22 and secured by small hose clamp 23. At the outlet end of tubing 24a is another ¼" male brass barbed fitting 22 and a small hose clamp 23. Fitting 22, attached to the outlet end of tubing 24a, is connected to a ¼" brass check valve 25 which blocks the passage of aqueous solution from spray tank 4 when the compressor is turned off while the tank remains under pressure. This protects the compressor's 6 diaphragm from the solution. Attached to the outlet end of check valve 25, is another ¼" male brass barbed fitting 22 which has approximately 28 inches of ³⁄₁₆" ID TYGON™ tubing 24b fastened to fitting 22 outlet end with another small hose clamp 23. The outlet end of tubing 24b is fastened to another ¼" male brass barbed fitting 22 with a small hose clamp 23. This fitting 22 is connected at its outlet end to a quick disconnect female 26 (female threads) which is mated with quick disconnect male 27 (female threads) which is an integral part of tank assembly 11 (FIG. 16) described below.

Figure 15:
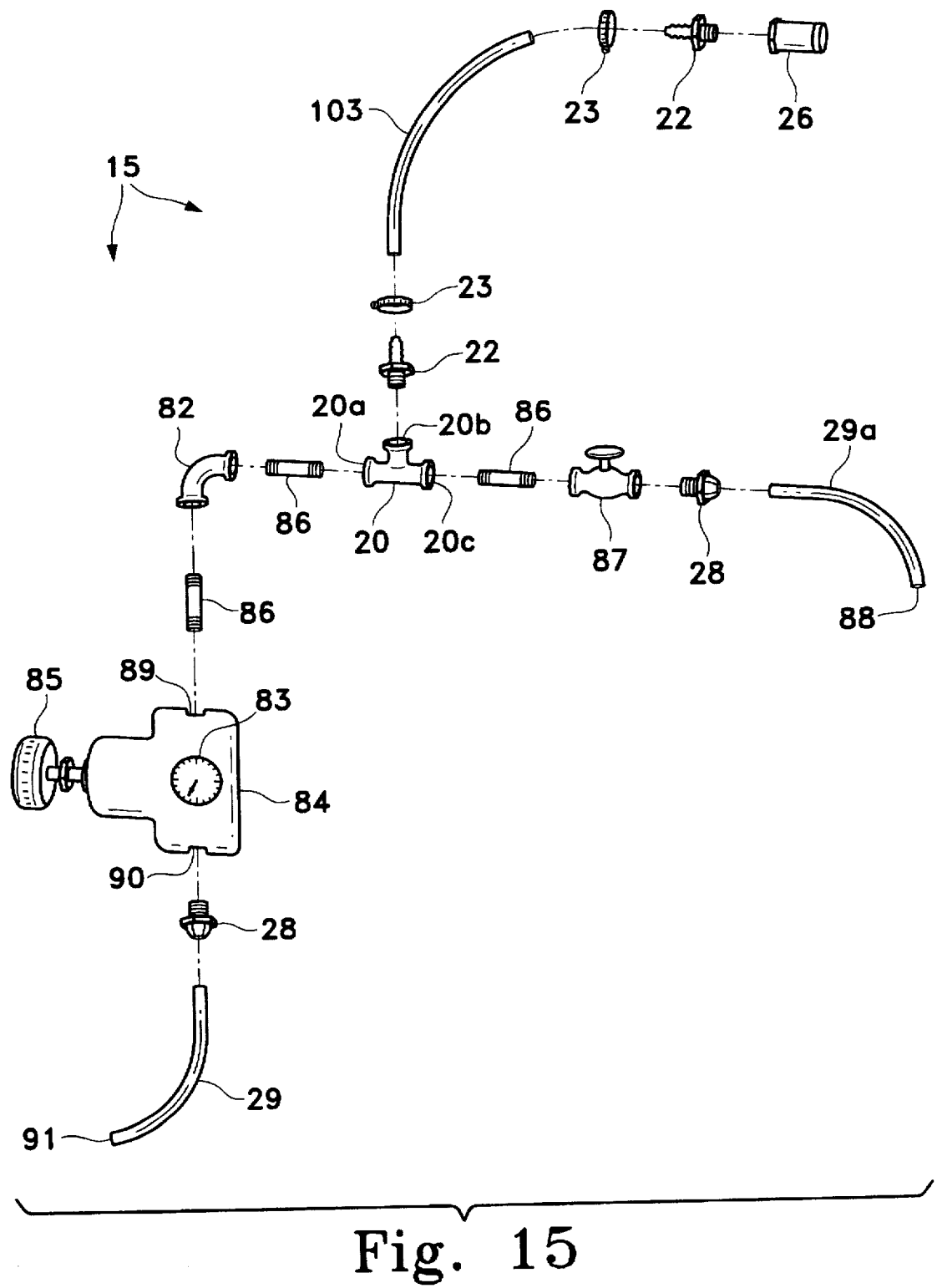
FIG. 15 is a perspective exploded view of pressure release system 15.

A bleed off system using a back-pressure regulator 84 that allows full throttle air into tank 4 for agitation while allowing the bleeding off of compressed air that is unnecessary to force the desired rate of aqueous solution out of the tank was designed in order to apply accurate rates of eggs onto target crops. Pressure release system 15 is shown in FIG. 15. A back pressure regulator 84 (0–60 PSI) (Bellofram Corporation, Newell, W. Va. 26050) is installed in the following manner: A ¼" galvanized nipple 86, approximately about 2½" in length, is threaded into inlet port 89 of regulator 84. A pressure gauge 83 (0–30 PSI) mounted on the regulator 84 serves as a reference point for back pressure settings when conducting multiple spray regimes on different crops or different rates of application. Control knob 85 is rotated clockwise to increase back pressure and counter clockwise to decrease back pressure. A ¼" galvanized elbow 82 is connected to the distal end of the first nipple 86. Another ¼" galvanized nipple 86 is threaded into the distal end of elbow 82. Threaded onto the distal end of the second nipple 86 is a ¼" galvanized tee 20 which serves as a point of junction for incoming compressed air bleeding off from tank 4 and the pressure release system 15. Inlet 20b of tee 20, located 90° from outlets 20a and 20c, is connected to a ¼" male brass barbed fitting 22. On the distal end of fitting 22 is approximately about 110 inches of 3/16" ID TYGON™ tubing 103 held in place by a small hose clamp 23. Inserted into the distal end of tubing 103, which is located on ESD 1, is another ¼" male brass barbed fitting 22, with tubing 103 held in place by another small hose clamp 23. A quick disconnect female 26 (female threads) is threaded onto the distal end of the second ¼" fitting 22. The quick disconnect female 26 is mated with a quick disconnect male 27a on tank 4 which places tank 4 in communication with the pressure release system 15. Connected to outlet 20c, of tee 20, is a ¼" ID galvanized nipple 86 which connects on its distal end to a ¼" pressure release needle valve 87. This valve serves as the means for depressurizing the whole system which is necessary before opening the fill port 47 of tank 4. This valve also allows back pressure regulator 84 to be set at a predetermined pressure setting which remains at the same setting after refilling tank 4. Connected to outlet side of valve 87 is a ¼" male ferrel adapter 28 which has approximately about 6 inches in length of ¼" OD copper tubing 29a attached to its distal end. Tubing 29a forms pressure release compressed air outlet port 88 at its distal end.

Connected to outlet port 90 of regulator 84 is a ¼" male ferrel adaptor 28 with approximately about 4 inches of ¼" OD copper tubing 29b. Tubing 29b forms compressed air bleed off port 91.

Tank assembly 11 (FIG. 16) is made up of three ports that allow pressurization and agitation-port 37, flow of aqueous solution—port 33a, and pressure bleed off for control of flow of aqueous solution—port 36a. Spray tank 4 is a commercially available 2 gallon hand pressurized spray tank (RL Flo-Master® Funnel Top Sprayer, RL Corp., Lowell, Mich. 49331) modified by removing the original hand pump assembly (not shown) from pump housing 43. Housing 43, which serves as the closing and seal of tank fill port 47, is modified in the following manner: A 1" diameter hole 48b is drilled in the botttom 48a of housing 43 (where the rubber check valve for the conventional hand pump was located) and ¼" plastic bung hole fitting 39 is inserted through hole 48b. The top 39a (male) of fitting 39 is inserted from inside housing 43 through hole 48b, extending outside housing 43, through rubber gasket 38 on the exterior bottom 48a of pump housing 43. Top 39a of fitting 39 then threads into the bottom 39b (female) of fitting 43. Threaded into top 39a of fitting 39 is a ¼" male ferrel adaptor 28 with approximately about 11¾ inches of ¼" OD copper tubing 29c attached to the outlet end. Tubing 29c extends upward through the hollow interior of pump housing handle 44, and extends approximately about 2" above the top of handle 44. A second ¼" male ferrel adapter 28 is connected to the exterior end of tubing 29c. A quick disconnect male (female threads) 27 is fastened to the inlet end of fitting 28. Disconnect 27 is mated to quick disconnect female 26 of compressed air system 18 (FIG. 14). Attached to outlet end of bottom 39b of fitting 39 is a ¼" male ferrel adapter 28 which has a ¼" OD copper tubing 29d, approximately about 1¼ inches in length, attached to the outlet end of adapter 28. Tubing 29d places compressed air outlet port 37 approximately about 3/16" from the inside bottom of spray tank 4 when pump housing 43 is inserted into tank fill port 47 and tightened until rubber seal 42 mates with molded depression (not shown) in fill port 47.

A ¼" plastic pick-up tube 33 and plastic adapter 34 are original parts of the hand sprayer and formerly served as the connection point of the original hose and wand. Aqueous solution inlet port 33a is formed by the inlet end of tube 33 which is attached to the inlet end of adapter 34. Attached to the barbed end of adapter 34 is 3/16" ID TYGON™ tubing 101, approximately about 110 inches in length, held in place by small hose clamp 23. The outlet end of tubing 101 is clamped by another small hose clamp 23 onto the barbed end of a ¼" male brass barbed fitting 22. The outlet end of fitting 22 is threaded into the inlet end of a ¼" brass ball valve 32 which serves as a flow control valve for the operation of the sprayer. Connected to the outlet end of valve 32 is another ¼" male brass barbed fitting 22. Attached to the outlet end of fitting 22 is a piece of 3/16" ID TYGON™ tubing 102, approximately about 146 inches in length, held into place by a small hose clamp 102. Tubing 102 is routed to the base of stand pipe 7 (FIG. 13a–13b) where a ³⁄₁₆" plastic union 45 (male) is attached. Union 45 is mated to a ³⁄₁₆" plastic union 46 (female) on aqueous solution system 16 or 17 (FIGS. 8a and 10).

Spray tank 4 is modified by drilling a ⅜" hole in the top shoulder of tank 4. A ¼" bulkhead fitting 36 is mounted in the hole and a quick disconnect male 27a (male threads) is attached to the outlet end of fitting 36. Quick disconnect 27a is mated with female quick disconnect 26 which is part of pressure release system 15, placing spray tank 4 in communication with pressure release system 15.

Remote control assembly 109 (FIGS. 17a, 17b, and 17c) is made up of (1) pressure release system 15, (2) ¼" brass valve 32 (the flow control), (3) heavy duty 12 VDC automotive toggle switch 96 (for 12 VDC compressor), (4) a light duty kill switch 97 (for gasoline engine driven blower fan), and (5) a remote throttle control 95 for the gasoline driven blower fan 5. All of 15, 32, 95, 96, and 97 are mounted on or contained in control panel box 92 which is approximately about 10"×10"×4". A 2" flexible covered electrical conduit 93 is attached to the remote control panel box 92 with a 2" flex/box connector 94. Remote control panel box 92 also receives a heavily insulated 12-2 electrical cable 105 with positive (+) and negative (−) alligator clips 16 which connect to the 12 VDC power source of a tractor, all-terrain vehicle (ATV) or any other vehicle suitable for spraying agricultural commodities. The positive lead (not shown) of cable 105 is connected to the heavy duty automotive toggle switch 96 through a 10 amp fuse link (not shown) in electrical junction box 108. With remote control panel box 92 mounted on the fender 111 of tractor 110 (right or left side, FIGS. 1–6, and 17c), the 2" flexible covered electrical conduit 93 is routed to the rear of tractor 110 and is attached to 6"×6"×3" electrical junction box 107 with a 2" ID flex/box connector 94. The 6"×6" 3" electrical junction box mounted on the front center of deck and framework 2 serves as a distribution point for all that is routed through conduit 93. The following components are routed through conduit 93 and link up remote control 109 with ESD 1: (1) a 110" length of ³⁄₁₆" ID TYGON™ tubing which is aqueous solution tubing 101 from spray tank 4 to ¼" brass ball valve 32; (2) a 146" length of ³⁄₁₆" ID TYGON™ tubing which is the aqueous solution return tubing 112 from brass ball valve 32; (3) a 110" length of ³⁄₁₆" ID TYGON™ tubing which is compressed air bleed off tubing 113 from spray tank 4 to pressure release system 15; (4) a throttle control cable 100 which connects throttle 95 to blower fan 5 engine; (5) two 12 gauge automotive electrical wires 98 from power source and heavy duty electrical toggle switch 96 to compressor 6; and (6) two 18 gauge automotive electrical wires 99 from light duty kill switch 97 to gasoline engine driven blower fan 5. Visual flow tubes 104 are the outlet end of tubing 101 and the inlet end of tubing 102 which are attached to the inlet and outlet ends of valve 32, respectively. Tubes 104 enable an operator to visually observe the flow of eggs through the tubing in case of a stopped up tube or other malfunction. From the distribution point, junction box 107 and cover 107a, each component is routed to the appropriate connection point as described above for each system. The only system that does not pass through the remote control assembly 109 is the compressed air system 18 which is routed directly from compressor 6 to spray tank 4 with ¼" brass check valve 25 mounted on cover 107a of junction box 107. Electrical wires 98 are routed from the distribution point of junction box 107 to a 4"×2"×2" electrical junction box 108 with cover 108a which is mounted onto motor housing 6a of compressor 6. The positive (+) leads of wires 98 pass through a 10 amp fuse link (not shown) before connecting up with the positive (+) lead of compressor 6. The fuse link serves as protection for the compressor against a power surge or a mistaken connection to a power source greater than 12 VDC.

The aqueous solution containing beneficial insect eggs is made up of a sticking agent, water, and beneficial insect eggs. The concentration of the sticking agent in water is from about 2% to about 25% for good to excellent adhesive properties, with a more preferred concentration of from about 2% to about 15% for achieving a high percentage of eggs hatching. The sticking agent can be any sprayable adhesive agent which is not toxic to the insect eggs and does not foul the sprayer. Examples of useful sticking agents are a starch-sucrose formulation, or a flour-sucrose formulation, both as disclosed in U.S. Pat. No. 5,061,697, which is herein incorporated by reference in its entirety; and Smucker Biocarrier (Smucker Manufacturing, Inc., 22919 No. Coburg Road, Harrisburg, Oreg. 97446). The beneficial insect eggs are used at a concentration of at least about 1,000 eggs per gallon. A limitation of the upper concentration range is the amount of eggs which will clog aqueous spraying system 16 or 17.

In operation, tractor 10 is driven between rows of agricultural commodities such as trees, grapes, tomatos, etc. as the aqueous solution containing beneficial insect eggs in tank 4 is being pumped into tubing 101 and 102, controlled by ¼" brass ball valve 32 via inlet port 35, and tubing 63 on into spraying arms 61 of aqueous solution systems 16 (Embodiments I and II) or 17 (Embodiment III) via male and female unions 45 and 46 on tubings 63 and 64a, respectively. The eggs and aqueous solution exit the aqueous solution arms 61 through ports 57 and are blown onto the plants by air forced through ports 56a or 66b of spraying arms 50, 67, or 72 of the three different air systems 12, 13, or 14. Throttle 95 controls the flow of air from blower fan 5 to the arms of the different air systems 12,13, or 14. In addition, pressurized air, from compressor 6, is pumped into tank 4 to pressurize the tank and to provide continuous agitation of the aqueous solution in order to keep the eggs in suspension whether tank 4 is filled or near empty. Furthermore, back pressure regulator 84 allows a full throttle of air from compressor 6 into tank 4 for agitation while allowing bleeding off of compressed air from tank 4, through bleed off port 91, which is necessary to force the desired rate of flow of aqueous solution out of tank 4 through aqueous solution inlet port 33a. Regulator 84 also allows for different rates of applications and pressure gauge 83 serves as a reference point for back pressure settings when conducting multiple spray regimes on different crops. Compressor 6 with blower fan 5 provides the air, through stand pipe 7 (air systems 12 or 13) or through Y-fitting 69 connected directly to blower fan 5 (air system 14), that flows through spraying arms 50, 67, or 72 of air systems 12, 13, or 14 and propels the aqueous solution with eggs, exiting from port 57, away from ESD 1 and onto the agricultural commodities. To shut down the system, compressor 6 is shut off by toggle switch 96 and the gasoline engine of blower 5 is shut off by kill switch 97 on remote control panel box 92. When compressor 6 is turned off, the pressure release valve 87 of pressure release system 15 is opened to relieve tank pressure. If this is not done the tank remains under pressure and check valve 25, of compressed air system 18, blocks the passage of aqueous solution from tank 4 to compressor's 6 diaphragm. To depressurize ESD 1 for refilling or for emptying tank 4 through port 47, pressure release valve 87, of pressure release system 15, is opened. Valve 87 also allows for rapid release and for back automatic return of preset pressure on aqueous solution systems 16 or 17 after refilling tank 4.

The following examples illustrate the invention and are not intended to limit the scope of the invention as defined by the claims. Lacewing eggs are used as a test model system.

EXAMPLE 1

Tests were performed to identify sticking agents which are non-toxic to lacewing eggs. Approximately about 6500 eggs were added to 100 ml of water containing adhesives at various concentrations for 15 minutes. The sticking agents were BOND, a spray adjuvant, spreader-sticker with surfactant, deposition agent (Loveland Industries, Inc., P.O. Box 1289, Greely, Colo. 80632); Plyac, a spray adjuvant, spreader-sticker (HACO, Inc., Box 7190, Madison, Wis. 53707); Intac, a spray enhancer and evaporation reducer (Loveland Industries, Inc.); and Smucker Biocarrier (Smucker Manufacturing, Inc., 22919 No. Coburg Road, Harrisburg, Oreg. 97446). Eggs were either randomly selected or preselected by removing abnormal eggs from pipetted samples of 3 ml, replicated five times. Eggs are considered abnormal if they a) are crushed, b) remain bright green after oviposition (probably infertile since these eggs never hatch), or c) are flattened because of dehydration. The results are shown below in Table 1.

TABLE I

| Test | Treatment | Ratio - Water:Adhesive | % Hatch | Adhesive Property |
|---|---|---|---|---|
| All eggs used | Water:Bond | 800:1 | 49 | Poor |
| | Water:Plyac | 800:1 | 37 | Poor |
| | Water:Intac | 64:1 | 41 | Poor |
| | Water:Smucker Biocarrier | 4:1 | 21 | Excellent |
| | Water | 1:0 | 46 | None |
| All eggs used | Water:Smucker Biocarrier | 8:1 | 50 | Good |
| All eggs used | Water:Smucker Biocarrier | 8:1 | 46 | Good |
| All eggs used | Water:Smucker Biocarrier | 8:1 | 56 | Good |
| Pre-selected | Water:Smucker Biocarrier (No Clorox) | 8:1 | 86 | Good |
| | Water:Smucker Biocarrier (Cloroxed eggs) | 8:1 | 90 | Good |
| | Dry (Cloroxed eggs) | — | 92 | — |
| | Water (Cloroxed eggs) | 1:0 | 88 | None |
| | Water (No Clorox) | 1:0 | 93 | None |
| | No Treatment | — | 86 | — |

Additional sticking agents were tested that include a flour-sucrose formulation or a starch-sucrose formulation as described in U.S. Pat. No. 5,061,697 incorporated by reference supra. Pregelatinized corn flour (12687, Illinois Cereal Mills, Inc.) or MIRA-SPERSE (industrial grade, C3-444, A. E., Staley Co.) are mixed 1:1 with sucrose (Domino Confectioners 10X Sugar, Amstar Sugar Corp.) and then dissolved in water to obtain a 2% or a 4% solution. Since both concentrations stick equally well (data not shown), the 2% solutions were tested for % egg hatch using 20 eggs in 100 ml (milliliters) of solution for time periods of 20–120 minutes. The results are shown below in Table II.

TABLE II

| | | % Egg Hatch | | |
|---|---|---|---|---|
| No. Eggs | Time in Solution (min.) | 2% Flour – Sucrose + Water | 2% Starch Sucrose + water | Water only |
| 20 | 20 | 75 | 90 | 40 |
| 20 | 40 | 95 | 95 | 85 |
| 20 | 60 | 80 | 90 | 95 |
| 20 | 80 | 100 | 90 | 85 |
| 20 | 100 | 75 | 70 | 90 |
| 20 | 120 | 60 | 85 | 75 |

Both formulations at either 2% or 4% in water solutions cause little mortality to the eggs and stick eggs better than the Smucker Biocarrier in Example 1 above. The two formulations, however, do not suspend eggs as well as Smucker Biocarrier. This is not a problem though because the spraying device constantly agitates the eggs in the sticking agent keeping the eggs well dispersed. Both the starch- and the flour-sucrose formulations are resistant to dissolution by rainfall (data not shown).

The foregoing detailed description is for the purpose of illustration. Such detail is solely for that purpose and those skilled in the art can make variations therein without departing from the spirit and scope of the invention.

INDEX OF THE ELEMENTS DESIGNATED BY A NUMERAL

1. Egg Spraying Device (ESD)
2. Deck and framework
3. 3-Point Hitch
4. Spray tank 2 gal.
5. Gasoline engine driven blower fan
6. Compressor 12 VDC Gast® Diaphragm Compressor
6a. Compressor Motor Housing
7. Stand pipe (2" ID/PVC)
8. Receiving Coupling 2" PVC (Embodiment, I, II, and III)
9. Rubber coupling w/clamps
10. PVC coupling/blower connector (2" PVC)
11. Tank Assembly
12. Air system for moderate height plants
13. Air system for trees
14. Air system for row crops
15. Pressure release system
16. Aqueous solution system (Embodiment I and III)
17. Aqueous solution system (Embodiment II)
18. Compressed air system
19. Air filter assembly
20. ¼" galvanized tee
20a. Outlet of ¼" galvanized tee 20
20b. Inlet of ¼" galvanized tee 20
20C. Outlet of ¼" galvanized tee 20
21. ¼" galvanized nipple (8")
22. ¼" male brass barbed fitting
23. Small hose clamp
24a. Compressed air line tubing from compressor to backflow valve (26" length of 3/16" ID TYGON™ tubing)
24b. Compressed air lien tubing from backflow valve to tank (28" length of 3/16" ID TYGON™ tubing)
25. ¼" brass check valve
26. Quick disconnect female (female threads)
27. Quick disconnect male (female threads)
27a. Quick disconnect male (male threads)
28. ¼" male ferrel adapter
29a. ¼" O.D. copper tubing (6" length)

29b. ¼" O.D. copper tubing (4" length)
29c. ¼" O.D. copper tubing,(11¾" length)
29d. ¼" O.D. copper tubing (1¼" length)
30. Air inlet
31. Air outlet
32. ¼" brass ball valve
33. ¼" Plastic pick-up (aqueous solution pickup) (part mfg. by Sprayer Co.)
33a. Port inlet of pick-up tube 33.
34. Special plastic adapter (part mfg. by Sprayer Co.) (came already installed on tank—spray hose connector)
36. ¼" Bulkhead fitting
36a. Pressure bleed-off port
37. Compressed air outlet port (pressurization and agitation)
38. Rubber gasket
39. ¼" plastic bung hole fitting
39a. Top of fitting (male)
39b. Bottom of fitting (female)
42. Rubber seal (part mfg. by Sprayer Co.)
43. Pump housing (part mfg. by Sprayer Co.; modified)
44. Pump housing handle
45. ³⁄₁₆" plastic union (male)
46. ³⁄₁₆" plastic union (female)
47. Tank fill port
48a. Bottom of pump housing
48b. Hole (1" d)
49. 2" PVC drain tee
49a. Inner end of tee
49b. Outer ends of tee
50. Spraying arms (air system 12)
50a. 2" ID PVC pipe (8" length)
51. 2" ID PVC pipe (2" length)
52. 2" ID PVC female adapters
53. 2" Greenfield, squeeze type, flex/box connector
54. 2" ID flexible exhaust pipe (10¾" length)
55. 2"—1½" PVC reducer bushing
56. Formed air outlet 1½" ID PVC pipe, cut across one end at 45°)
56a. Air outlet ports (1½")
56b. Longitudinal slot
57. Outlet port (aqueous solution)
58. 6 mm plastic barbed Y-fitting
58a. Inlet port
58b. Outlet port
59. Small threaded plug
60. ³⁄₃₂" I.D. Tygon™ tubing (1" length)
61. Arm of aqueous solution system (air systems 12, 14)
61a. ⅛" I.D. Tygon™ tubing (30" length)
62. 8 mm plastic barbed Y-fitting
62a. Inlet port
62b. Outlet port
63. ³⁄₁₆" ID Tygon™ tubing (2½" length)
64. Arm of aqueous solution system (air system 13)
64a. ⅛" ID TYGON™ tubing (21" length)
66. Formed air outlet 2" PVC pipe, cut across one end at 45°
66a. Longitudinal slot
66b. Air outlet port (2")
67. Spraying arm
67a. 2" flexible exhaust pipe (12" length)
69. 2" PVC Y-fitting
69a. Inlet out
69b. Outlet ports
70. 2" PVC coupling, female threaded/female glue joint
71. 2" plastic male barbed fitting
72. Spraying arms
72a. 2" flexible plastic hose
73. Medium size hose clamps
74. Modified 2" galvanized coupling
74a. Wall of galvanized coupling
74b. Carriage bolts
75. Mounting assembly (Embodiment III)
76. Stand pipe brace
77. Electrical strut system channel
77a. Lips of channel
77b. Open side
78. 3"×4" u-bolts
79. Slide bar assembly
80. ¼" stock aluminum bar (4"×1¼")
80a. 1"×3/8" machine bolts
81. 2"×2"×¼" aluminum angle (4" length)
81a. Top of angle
82. ¼" galvanized elbow
83. Pressure gauge (0–30 PSI)
84. Back pressure regulator (0–60 PSI)
85. Control knob (back pressure regulator)
86. ¼" galvanized nipple (2" length)
87. ¼" pressure release needle valve
88. Pressure release compressed air outlet port
89. Inlet port of the regulator
90. Outlet port of the regulator
91. Compressed air bleed off port
92. Remote control panel box
93. 2" flexible covered electrical conduit
94. 2" flex/box connector
95. Remote throttle control
96. Heavy duty 12 VDC automotive toggle switch
97. Light duty kill switch
98. 12 ga. automotive electrical wire
99. 18 ga. automotive electrical wire
100. Throttle control cable
101. Aqueous solution tubing from spray tank
102. Aqueous solution return tubing
103. Compressed air bleed off tubing
104. Visual flow tubes (sight gauge for visual observation of aqueous solution and eggs)
105. Heavily insulated 12-2 electrical cable
106. Alligator clips (battery post connectors)
107. 6"×6"×3" electrical junction box
107a. Junction box cover
108. 4"×2"×2" electrical junction box
108a. Junction box cover
109. Remote control assembly
110. Tractor
111. Fender

We claim:

1. A device comprising an air system selected from the group consisting of an air system for spraying agricultural commodities of moderate height, an air system for spraying trees and an air system for spraying row crops, an aqueous solution system for delivering intact, viable insect eggs to agricultural commodities wherein an outlet port of said aqueous solution system inserts into an outlet port of said air system, a spray tank assembly in fluid communication with said aqueous solution system, a compressed air system in fluid communication with said spray tank assembly for pressurizing a spray tank in said spray tank assembly and providing continuous agitation of an aqueous solution comprising viable beneficial insect eggs in said spray tank in order to keep said eggs in suspension, and a pressure release assembly in communication with said spray tank assembly;

wherein said device sprays intact, viable beneficial insect eggs onto agricultural commodities.

2. The device of claim 1 wherein said aqueous solution system is selected from the group consisting of an aqueous solution system for spraying trees or moderate height commodities and an aqueous solution system for spraying row crops.

3. The device of claim 1 wherein said pressure release system comprises a back pressure regulator.

4. The device of claim 1 wherein said compressed air system comprises a compressor.

5. The device of claim 1 further comprising a remote control assembly.

6. The device of claim 1 further comprising an aqueous suspension that includes a sticking agent and beneficial insect eggs.

7. The device of claim 6 wherein said sticking agent is selected from the group consisting of Smucker Biocarrier, a flour-sucrose formulation, and a starch-sucrose formulation.

8. A method for attaching beneficial insect eggs to agricultural commodities comprising spraying an aqueous suspension containing beneficial insect eggs onto said commodities using the device of claim 1.

9. A method comprising filling a spray tank with an aqueous suspension comprising a sticking agent and viable beneficial insect eggs, continually mixing said viable eggs in said suspension in said spray tank by pumping into said tank pressurized air from a compressor, propelling said aqueous suspension containing said viable eggs through an aqueous suspension system and out at least one port of said aqueous system by increasing air pressure in said spray tank, and blowing said viable insect eggs in said suspension onto agricultural commodities as they exit from said ports with air exiting an outlet port in an air system and said air is from a blower fan and said aqueous solution system comprises an outlet port which inserts into said air system outlet port, and controlling pest insects on said commodities by hatching said beneficial insect eggs blown onto said commodities.

* * * * *